United States Patent
Jain et al.

(10) Patent No.: US 9,622,977 B2
(45) Date of Patent: Apr. 18, 2017

(54) SUSTAINED RELEASE DRUG DELIVERY SYSTEM

(75) Inventors: Subheet Jain, Punjab (IN); Sumeet Dhaliwal, Punjab (IN); Madhu Rana, Punjab (IN); Hardevinder Pal Singh, Punjab (IN); Ashok Kumar Tiwary, Punjab (IN)

(73) Assignee: BIOPLUS LIFE SCIENCES PVT, LTD., Karnataka (IN)

( * ) Notice: Subject to any disclaimer, the term of this patent is extended or adjusted under 35 U.S.C. 154(b) by 0 days.

(21) Appl. No.: 13/123,034

(22) PCT Filed: Oct. 8, 2009

(86) PCT No.: PCT/IN2009/000562
§ 371 (c)(1),
(2), (4) Date: Jun. 15, 2011

(87) PCT Pub. No.: WO2010/041279
PCT Pub. Date: Apr. 15, 2010

(65) Prior Publication Data
US 2011/0244034 A1    Oct. 6, 2011

(30) Foreign Application Priority Data
Oct. 8, 2008  (IN) .......................... 2158/MUM/2008

(51) Int. Cl.
| A61K 9/00 | (2006.01) |
| A61K 31/522 | (2006.01) |
| A61K 9/22 | (2006.01) |
| A61K 9/52 | (2006.01) |
| A61P 31/22 | (2006.01) |
| A61K 9/20 | (2006.01) |
| A61K 9/16 | (2006.01) |

(52) U.S. Cl.
CPC ............ *A61K 9/205* (2013.01); *A61K 9/0065* (2013.01); *A61K 9/1652* (2013.01); *A61K 31/522* (2013.01)

(58) Field of Classification Search
CPC .... A61K 9/0065; A61K 31/522; A61K 9/205; A61K 9/1652
See application file for complete search history.

(56) References Cited

U.S. PATENT DOCUMENTS

| 6,120,803 A * | 9/2000 | Wong et al. ................. 424/473 |
| 6,340,475 B2 | 1/2002 | Shell et al. |
| 6,548,083 B1 | 4/2003 | Wong et al. |
| 2002/0119192 A1* | 8/2002 | Vishwanathan et al. ..... 424/461 |
| 2003/0091630 A1* | 5/2003 | Louie-Helm et al. ........ 424/468 |
| 2004/0185105 A1 | 9/2004 | Berner et al. |
| 2004/0219186 A1* | 11/2004 | Ayres ............................. 424/426 |
| 2007/0160678 A1 | 7/2007 | Guimberteau et al. |

FOREIGN PATENT DOCUMENTS

| EP | 1382331 | 1/2004 |
| EP | 1382331 A1 | 1/2004 |
| KR | 2001-0012857 A | 2/2001 |
| WO | 98/52547 A1 | 11/1998 |
| WO | 01/10405 | 2/2001 |
| WO | 01/97783 | 12/2001 |
| WO | 01/97783 A1 | 12/2001 |
| WO | 03/035029 | 5/2003 |
| WO | 03/097014 | 11/2003 |
| WO | 03/097018 | 11/2003 |
| WO | 2005/079752 | 9/2005 |
| WO | 2007/000778 | 1/2007 |
| WO | 2008/131506 | 11/2008 |
| WO | 2009/153632 | 12/2009 |

OTHER PUBLICATIONS

Dhaliwal et al (published online Jun. 4, 2008). "Mucoadhesive Microspheres for Gastroretentive Delivery of Acyclovir: In Vitro and In Vivo Evaluation". The AAPS Journal, 10(2): 322-330.*
Lubrizol (May 31, 2010). "Lubrizol Pharmaceutical Polymers for Controlled Release Tablets and Capsules". Pharmaceutical Bulletin 30: 1-7.*
Guggi D., et al., "Comparative evaluation of cytotoxicity of glucosamine-TBA conjugate and a chitosan-TBA conjugate," International Journal of Pharmaceuticals 278, pp. 353-360 (2004).
Hu, F., et al., "Cellular uptake and cytotoxicity of shell crosslinked stearic acid-grafted chitosan oligosaccharide micelles encapsulating doxorubicin," European Journal of Pharmaceutics and Biopharmaceutics, (2007).
Maculotti K, et al, "Preparation and in vitro evaluation of thiolated chitosan microparticles," Journal of Microencapsulation 22(5), pp. 459-470, (2005).

(Continued)

*Primary Examiner* — Anoop Singh
*Assistant Examiner* — Doan Phan
(74) *Attorney, Agent, or Firm* — Knobbe, Martens, Olson & Bear LLP

(57) ABSTRACT

Controlled release dosage forms comprising a pharmaceutically active agent capable of not more than 90% release in 12 hours in a simulated gastric juice in first order release rate USP type 1 dissolution test, comprising (a) a tablet made from polymer matrix of at least two biocompatible polymers, the pharmaceutically active agent and excipients; the tablet capable of rapid swelling without disintegration in simulated gastric juice to a size resulting in gastric retention in the stomach and controlled release of the active agent by controlled erosion and diffusion immediately after coming into contact with the gastric juice, or (b) microspheres of ungrafted chitosan or a chitosan derivative or CARBOPOL® incorporating the active agent which is not a polymeric molecule and after administration in stomach, the microspheres adhere to the gastric mucosa for a long and controlled time release of the active agent.

3 Claims, 17 Drawing Sheets

(56) References Cited

OTHER PUBLICATIONS

Figure 1:
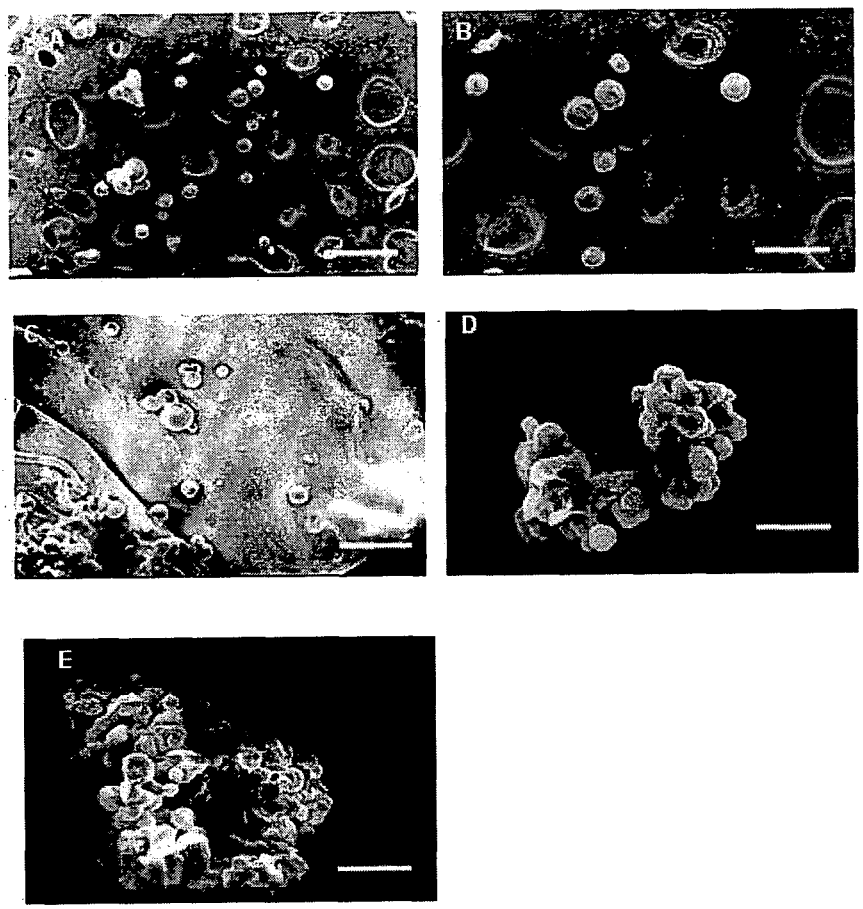

Kotze, A.F., et al., " N-trimethyl chitosan chloride as a potential absorption enhancer across mucosal surfaces: In vitro evaluation in intestinal epithelial cells (Caco-2)," Pharmaceutical Research, vol. 14, No. 9, pp. 1197-1202, (1997).
Artursson P, et al., "Effect of chitosan on permeability of monolayers of intestinal epithelial cells (Caco-2)," Pharmaceutical Research, vol. 11, No. 9, pp. 1358-1361 (1994).
Kotze, A.F., et al., "Enhancement of paracellular drug transport with highly quaternized N-trimethyl chitosan chloride in neutral environments: In vitro evaluation in intestinal epithelial cells (Caco-2)," Journal of Pharmaceutical Sciences, vol. 88, No. 2, pp. 253-257 (1999).
Bernkop-Schnurch, A., et al., "Polymers with Thiol groups: A new generation of mucoadhesive polymers?" Pharmaceutical Research, vol. 16, No. 6, pp. 876-881 (1999).
Bernkop-Schnurch A., et al., "Thiolated polymers-thiomers: synthesis and in vitro evaluation of chitosan-2-iminothiolane conjugates," International Journal of Pharmaceutics, vol. 260, pp. 229-237, (2003).
Ruhnek-Forsbeck, M., et al., "Treatment of recurrent genital herpes simplex infection with oral acyclovir," Journal of Antimicrobial Chemotherapy, vol. 16, pp. 621-628 (1985).
Meadows K. C., et al., " Mechanism of acyclovir uptake in rat jejunum," Pharmaceutical Research, vol. 7, No. 3,299-303 (1990).
Wang, Y.M., et al., "Optimization of the formulation design of chitosan microspheres containing cisplatin," Journal of Pharmaceutical Sciences 1996; 85: 1204-1210.
Darwish, I.A., et al., "Simple fluorimetric method for determination of certain antiviral drugs via their oxidation with cerium(IV)," Il Farmaco 60, pp. 555-562 (2005).
Vys, S.P., et al., "An erythrocyte based bioadhesive system for nasal delivery of propranolol," Journal of Controlled Release 23, pp. 231-237 (1993).
Jain, S.K., et al., "Design and development of multivesicular liposomal depot delivery system for controlled systemic delivery of acyclovir sodium," AAPS PharmSciTech 6(1), pp. E35-E41 (2005).
Alireza, S., et al., "An investigation into the role of water movement and mucus gel dehydration in mucoadhesion," Journal of Controlled Release 25, pp. 197-203, (1993).
Fischer, D., et al., "In vitro cytotoxicity testing of polycations: influence of polymer structure on cell viability and hemolysis," Biomaterials 24, pp. 1121-1131 (2003).
Lewis, L.D., et al., Human gastrointestinal absorption of acyclovir from tablet duodenal infusion and sipped solution; Br. J. Clin. Pharmac 21, pp. 459-462 (1986).
US Prescribing information of Zovirax®, 8 pages.
Harikarnpakdee, S., et al., "Spray dried mucoadhesive microspheres: Preparation and transport through nasal cell monolayer," AAPS PharmSciTech 7(1): Article 12 (2006).
Leitner, V.M., et al., "Thiolated polymers: evidence for formation of disulphide bonds with mucus glycoproteins," European Journal of Pharmaceutics and Biopharmaceutics 56, pp. 207-214 (2003).
Bernkop-Schnurch, A., et al., "Thiolated chitosans: development and in vitro evaluation of a mucoadhesive, permeation enhancing oral drug delivery system," Journal of Control Release 94, 177-186 (2004).
Thanou, M., et al., "Chitosan and its derivatives as intestinal absorption enhancers," Advanced Drug Delivery Reviews 50, pp. S91-S101 (2001).
Rokhade, A.P., et al., "Novel interpenetrating polymer network microspheres of chitosan and methylcellulose for controlled release of theophylline," Carbohydrate Polymers 69(4), pp. 678-687 (2007).
Rokhade, A.P., et al., "Synthesis and characterization of semi-interpenetrating polymer network microspheres of acrylamide grafted dextran and chitosan for controlled release of acylovir," Carbohydrate Polymers (2006).
Thanou, M., et al., "Effects of N-Trimetyl chitosan chloride, a novel absorption enhancer, on Caco-2 intestinal epithelia and the ciliary beat frequency of chicken embryo trachea," International Journal of Pharmaceutics 185, pp. 73-82 (1999).
Kotze, A.F., et al., "Comparison of the effect of different chitosan salts and N-trimethyl chitosan chloride on the permeability of intestinal epithelial cells (Caco-2)," Journal of Controlled Release 51, pp. 36-46, (1998).
Genta, I., et al., "Bioadhesive Microspheres for Ophthalmic Administration of Acyclovir," J. Pharm. Pharmacol., vol. 49, pp. 737-742, (1997).
Maculotti, K, et al., "Preparation and in vitro evaluation of thiolated chitosan microparticles," Journal of Microencapsulation, vol. 22, No. 5, pp. 459-470 (2005).
Wagstaff, A., et al., "Aciclovir a Reappraisal of its Antiviral Activity, Pharmacokinetic Properties and Therapeutic Efficacy," Drugs, vol. 47, No. 1, pp. 153-205 (1994).
O'Brien, J., et al, "Acyclovir an Updated Review of its Antiviral Activity, Pharmacokinetic Properties and Therapeutic Efficacy," Drugs, vol. 37, pp. 233-309 (1989).
Thanoo, B., et al., "Cross-linked Chitosan Microspheres: Preparation and Evaluation as a Matrix for the Controlled Release of Pharmaceuticals," J. Pharm. Pharmacol., vol. 44, pp. 283-286 (1992).
Mortazavi, S., et al., "An investigation into the role of water movement and mucus gel dehydration in mucoadhesion," Journal of Controlled Release, vol. 25, pp. 197-203 (1993).
Dhaliwal et al., "Mucoadhesive Microspheres for Gastroretentive Delivery of Acyclovir: In Vitro and In Vivo Evaluation", The AAPS Journal, (2008), vol. 10, No. 2, pp. 322-330.
Korean Intellectual Property Office, Notice of Preliminary Rejection, Application No. 10-2011-7010514, dated Jun. 14, 2013, nine (9) pages.
First Official Action issued for Chinese Patent Application No. 200980140227.3 on Aug. 21, 2012. English translation attached.
Second Official Action issued for Chinese Patent Application No. 200980140227.3 on Apr. 9, 2013. English translation attached.
Supplemental European Search Report issued by the EPO for Patent Application No. 09818892.3 on Mar. 14, 2013.
Official Action issued by the Eurasian Patent Office for Eurasian Patent Application No. 201170529 / 28 on Oct. 31, 2012.
Written Opinion issued by the Hungarian Intellectual Property Office for Patent Application No. 2011025236 on May 25, 2012.
Preliminary Conclusion issued by the Ukrainian Industrial Property Institute for Registration Patent Application No. a201105754 on Dec. 11, 2012.
First Official Action issued for Japanese Patent Application No. 2011-530630 on May 21, 2013. English translation attached.
Patel J K & Patel M M, "Stomach Specific Anti-Helicobacter Pylori Therapy; Preparation and Evaluation of Amoxicillin-Loaded Chitosan Mucoadhesive Microspheres", Current Drug Delivery, 2007, vol. 4, No. 1, pp. 41-50.
Majithiya R J & Ramchandra R S M, "Chitosan-Based Mucoadhesive Microspheres of Clarithromycin as a Delivery System for Antibiotic to Stomach", Current Drug Delivery, 2005, vol. 2, No. 3, pp. 235-242.
Office Action issued in Chinese Application No. 200980140227.3 dated Nov. 27, 2013, 4 pages. English translation attached.
U.S. Department of Health and Human Services, "Guidance for Industry, Q8(R2) Pharmaceutical Development", Nov. 2009.
Fuertes, et al., "Estimation of the Percolation Thresholds in Acyclovir Hydrophilic Matrix Tablets", European Journal of Pharmaceutics and Biopharmaceutics, vol. 64, pp. 336-342, 2006.
Australian Patent Application No. 2009301994, Patent Examination Report dated Jan. 23, 2015, five (5) pages.
Australian Patent Application No. 2009301994, Patent Examination Report No. 2, dated Feb. 3, 2016, 4 pages.
First Examination Report, issued in Indian Patent Application No. 889/MUMNP/2011, dated Jan. 11, 2016, 2 pages.
Office Action dated Jun. 29, 2016 for European Application No. 09 818 892.3, 5 pages.
Rowe, et al., "Povidone", 2006, Handbook of Pharmaceutical Excipients, XP003024361.

* cited by examiner

SUSTAINED RELEASE DRUG DELIVERY SYSTEM

This is a National Phase Application filed under 35 U.S.C. 371 as a national stage of PCT/IN2009/000562, filed on Oct. 8, 2009 and claims benefit from Indian Patent Application No. 2158/MUM/2008, filed on Oct. 8, 2008, the entire content of which is hereby incorporated by reference in its entirety.

TECHNICAL FIELD

The present invention describes sustained/controlled drug delivery system so as to increase the bioavailability of a drug use of mucoadhesive, swelling polymers and their derivatives as a carrier for achieving sustained/controlled drug delivery, particularly for the drug acyclovir and the mucoadhesive swelling polymers like CARBOPOL® (High molecular weight, non-linear polyacrylic acid cross-linked with polyalkenyl polyether), PEO, Sodium alginate, Hypromellose, hydroxypropyl cellulose, sodium carboxy methyl cellulose, EUDRAGIT® (Poly(meth)acrylates), Chitosan and its derivatives.

BACKGROUND OF INVENTION

Some of the drug and macromolecules are poorly absorbed across the mucosal membrane or those that are sparingly/slowly soluble resulting in the fact that during limited time they remain in the gastrointestinal tract, enough of them is not released or absorbed and major portion passes out unabsorbed. One of the greatest challenge to the scientists is drug delivery of such molecules which show poor bioavailability as limited amount of the dose reaches the plasma in a specified period. Low bioavailability leads to variation in the drug absorption amongst the patients and become very difficult to administer the effective dosage. Hence, it has been a long awaited requirement of the drug delivery scientists to enhance the bioavailability of the such orally administered drugs. It was thought that a carrier which can deliver drug in intact form at target site, stays there for prolonged time and increases the permeability of the mucosal membrane to achieve unhampered and better absorption of the drug shall be a remedy, provided the carrier is safe and does not affect the properties of the mucosal epithelium. Acyclovir, one of the subject matters of present invention is a drug in this category: poorly water soluble, has poor and variable oral bioavailability (10-20%), the elimination half-life of aciclovir is approximately 3 hours, is renally excreted, partly by glomerular filtration and partly by tubular secretion.

The present invention deals with carriers, including but not limited to polymers like chitosan (and its derivatives not limited to Thiolated chitosan, Trimethyl chitosan, hypermellose, polyethylene oxide, CARBOPOL®, sodium alginate, sodium carboxymethyl cellulose, xanthan gum and similar products, derivatives of these polymers, their various combinations and the like which are mucoadhesive, swellable and which increases the G.I. retention, bioavailability of the drug during the delivery.

PRIOR ART

Genta el al.[1] (1997)[1] have described use of microparticles of polylactides and polylactide-co-glycolide to achieve sustained delivery of acyclovir.

Thanau et al.[2] (2001) have extensively reviewed methods of use of chitosan and trimethyl chitosan as absorption enhancers of hydrophilic macromolecular drugs including peptide drugs. The experiments conducted in pigs and rats showed increased bioavailability of a peptide drug.

There are several examples of use of thiolated chitosan and TMC as drug delivery vehicle of macromolecular polymeric drugs such as insulin, laminin peptide, FITC-dextran 4000 as model lipophilic drug[3-5].

Grafted chitosans have been used as absorption enhancers in drug delivery systems.

Rokhade et al.[6] (2007) have described semi-interpenetrating polymer network (IPN) of microspheres of acrylamide grafted on dextran and chitosan prepared by emulsion cross-linking method using glutaraldehyde as a cross linker and encapsulation of acyclovir into the microspheres and drug release was found to be extended up to 12 hours. They have, however, used the drug theophylline and its physicochemical properties are totally different than Acyclovir in view of the fact that its bioavailability is 100%.

Hu et al.[7] (2009) have used stearic acid grafted chitosan oligosaccharide which form micelle wherein the drug is incorporated for improved absorption of the drug Doxorubicin.

U.S. Pat. No. 6,340,475[8] discloses a controlled-release oral drug dosage form for releasing a drug whose solubility in water is greater than one part by weight of said drug in ten parts by weight of water, said dosage form comprising a solid polymeric matrix with said drug dispersed therein at a weight ratio of drug to polymer of from about 15:85 to about 80:20, said polymeric matrix being one that swells upon imbibition of water thereby attaining a size large enough to promote retention in the stomach during said fed mode, that releases said drug into gastric fluid by the dissolution and diffusion of said drug out of said matrix by said gastric fluid, that upon immersion in gastric fluid retains at least about 40% of said drug one hour after such immersion and releases substantially all of said drug within about eight hours after such immersion, and that remains substantially intact until all of said drug is released. In other claims that pertain to several groups and examples of drugs, the claims limit the period required for release of substantially all of the said drug to within about 10 hours. In this patent the dosage form is designed for treating the local disease of stomach like Ulcer not for systemic absorption.

US 20040185105[9] discloses a controlled release dosage form comprising a polymer matrix and a pharmacologically active agent dispersed in the said polymer matrix comprised of a biocompatible, hydrophilic polymer where the dosage form upon imbibition of water swells unrestrained dimensionally to a size effective to promote gastric retention and maintains its size for an extended period of time before it is diminished by erosion.

US20070160678[10] discloses the invention of microcapsules of polymer insoluble in GIT fluid. The in vivo release pattern of acyclovir has also been described. Invention showed that 80% acyclovir was released in first 3 hrs. There is no information on the bioavailability and reduction of dosing frequency.

None of the above cited references describe in vivo studies conducted to know exactly how the drug works in the in vivo atmosphere. The present invention along with disclosure on novel and improved ways to use of various mucoadhesive carriers used to deliver drugs having low bioavailability describes in vitro as well as in vivo studies on controlled release compositions conducted and illustrated more particularly on a drug acyclovir entrapped in chitosan, thiolated chitosan and Trimethyl chitosan.or acyclovir associated with other polymers to achieve an objective of improving the uniformity of drug release and to increase the period for which the drug is released from the dosage form. The methods and compositions of this invention illustrated on Acyclovir are applicable on any other drug having same or similar properties as well as problems in the context of drug delivery, efficacy and treatment.

SUMMARY OF INVENTION

The invention discloses a controlled release dosage form comprising a therapeutically effective amount of a pharmaceutically active agent that would release in about 12 hours not more than about 90% of the said active agent in a simulated gastric juice in a first order rate of release in a USP type 1 dissolution test, and not containing a solubilizer or a swelling enhancer or both, comprising (a) a tablet made from polymer matrix of at least two biocompatible polymers, at least one of which is mucoadhesive, the said pharmaceutically active agent and pharmaceutically permitted excipients; the said tablet capable of rapid swelling without disintegration in the said simulated gastric juice to a size that shall result in its gastric retention in the stomach and start controlled release of the said active agent by starting controlled erosion immediately after coming into contact with the said gastric juice, or (b) microspheres of ungrafted chitosan or a chitosan derivative, or CARBOPOL® incorporating the said active agent, wherein the said pharmaceutically active agent is not a polymeric molecule and after administration in stomach, the said microspheres adhere to the gastric mucosa for a long time releasing the active agent in a controlled way. The two polymers illustrated in the tablet of this invention are CARBOPOL® 974P (High molecular weight polymer of acrylic acid crosslinked with allyl ethers of pentaerythritol) and Polyethylene oxide; however, any other pair of polymers can be used that shall result, in an appropriate proportion that have the drug release characteristics defined above. The permitted pharmaceutical excipients of this invention comprise a binder, a diluent, a pH modifier, a glidant, a lubricant, a film former, an anti-adherent, a coating agent, a colorant.

In one particular illustration of this invention, the tablet comprises Acyclovir, CARBOPOL® 974P, Polyethylene oxide, AVICEL® PH 101 (microcrystalline cellulose), POVIDONE® K30 (polyvinylpyrrolidone having the viscosity of 44000-54000), Magnesium stearate, and Colloidal silicon oxide. More particularly, the said tablet contains following ingredients for every 1000 mg of the dosage form: Acyclovir in amount 763.37 mg, CARBOPOL® 974P in amount 75 mg, Polyethylene oxide in amount 25 mg, AVICEL® PH 101 in amount 93.83 mg, POVIDONE® K30 in amount 30 mg, Magnesium stearate in amount 7.5 mg, Colloidal silicon oxide 5.0 mg.

The chitosan derivative used in making microspheres comprise Trimethyl chitosan or Thiolated chitosan. Mixtures may also be used, if expedient to achieve the desired drug release profile.

The microspheres of this invention may be packed in a sachet or are used as an ingredient with optional addition of permitted pharmaceutical ingredients and excipients to make a solid unit dosage form comprising a tablet or/and a capsule.

This invention also discloses a method of orally administering a therapeutically effective amount of a pharmaceutically active agent from a controlled release dosage form to a patient, the said dosage form would release in about 12 hours not more than about 90% of the said active agent in a simulated gastric juice in a first order rate of release in a USP type 1 dissolution test, and not containing a solubilizer or a swelling enhancer or both, comprising (a) a tablet made from polymer matrix of at least two biocompatible polymers, the said pharmaceutically active agent and pharmaceutically permitted excipients; the said tablet capable of rapid swelling without disintegration in the said simulated gastric juice to a size that shall result in its gastric retention in the stomach and start controlled release of the said active agent by starting controlled erosion immediately after coming into contact with the said gastric juice, or (b) microspheres of ungrafted chitosan or a chitosan derivative incorporating as the said active agent, wherein the said pharmaceutically active agent is not a polymeric molecule and after administration in stomach, the said microspheres adhere to the gastric mucosa for a long time releasing the active agent in a controlled way.

The polymers used in the method of this invention illustrated in this invention comprise CARBOPOL® 974P and Polyethylene oxide. However, any other pair of polymers providing the defined drug release profile as above may be used in their place.

The pharmaceutical active illustrated for method of this invention is Acyclovir. However, any other pharmaceutically active agent with same properties as Acyclovir and same drug release problems as Acyclovir may be used in its place.

The permitted pharmaceutical excipients used in the method of this invention comprise a binder, a diluent, a pH modifier, a glidant, a lubricant, a film former, an anti-adherent, a coating agent, a colorant.

The controlled release dosage form of the method of this invention comprises Acyclovir, CARBOPOL® 974P, Polyethylene oxide, AVICEL® PH 101, POVIDONE® K30, Magnesium stearate, Colloidal silicon oxide, Ethanol.

In a particular embodiment of method of this invention, every 1000 mg of the dosage form the said controlled release dosage form comprises Acyclovir in amount 763.37 mg, CARBOPOL® 974P in amount 75 mg, Polyethylene oxide in amount 25 mg, AVICEL® PH 101 in amount 93.83 mg, POVIDONE® K30 in amount 30 mg, Magnesium stearate in amount 7.5 mg, Colloidal silicon oxide in amount 5.0 mg.

Chitosan derivative used in making microspheres of this invention comprises Trimethyl chitosan or/and Thiolated chitosan.

This invention also comprises a method wherein the said microspheres are packed in a sachet or are used as an ingredient with optional addition of other pharmaceutically permitted ingredients and excipients to make a solid unit dosage form comprising a tablet and a capsule.

A process of making oral dosage form of this invention comprises, for tablet form, the steps of making wet granulation of a mixture comprising the said pharmaceutically active ingredient, the polymers and excipients, adding a gliadent and pressing into a tablet.

A process for making microspheres of this invention comprises preparing a solution of chitosan or a chitosan derivative in acetic acid, adding aqueous solution of the pharmaceutically active agent, adding this mixture to continuous phase consisting of light liquid paraffin and heavy liquid paraffin (1:1) containing a surfactant under constant stirring to form a water-in-oil emulsion, adding gluteraldehyde drop wise over a period of time, continuing stirring for a period of time, separating the microspheres formed by centrifugation, washing with petroleum ether to remove liquid paraffin, suspending in a sodium bisulfite solution and stirring for a period of time to remove residual gluteraldehyde, washing finally with distilled water, drying the microspheres.

BRIEF DESCRIPTION OF FIGURES AND LEGENDS

FIG. 1. SEM photomicrograph of Chitosan (A), N-TMC (B), Thiolated chitosan (C), CARBOPOL® (D) and METHOCEL® K15M (cellulose ether) (E) microsphere (X 10,000). Scale bar=50 μm FIG. 2. % Swelling measurement of microspheres formulations. Data are represents as mean±SD (n=3)

Figure 3:
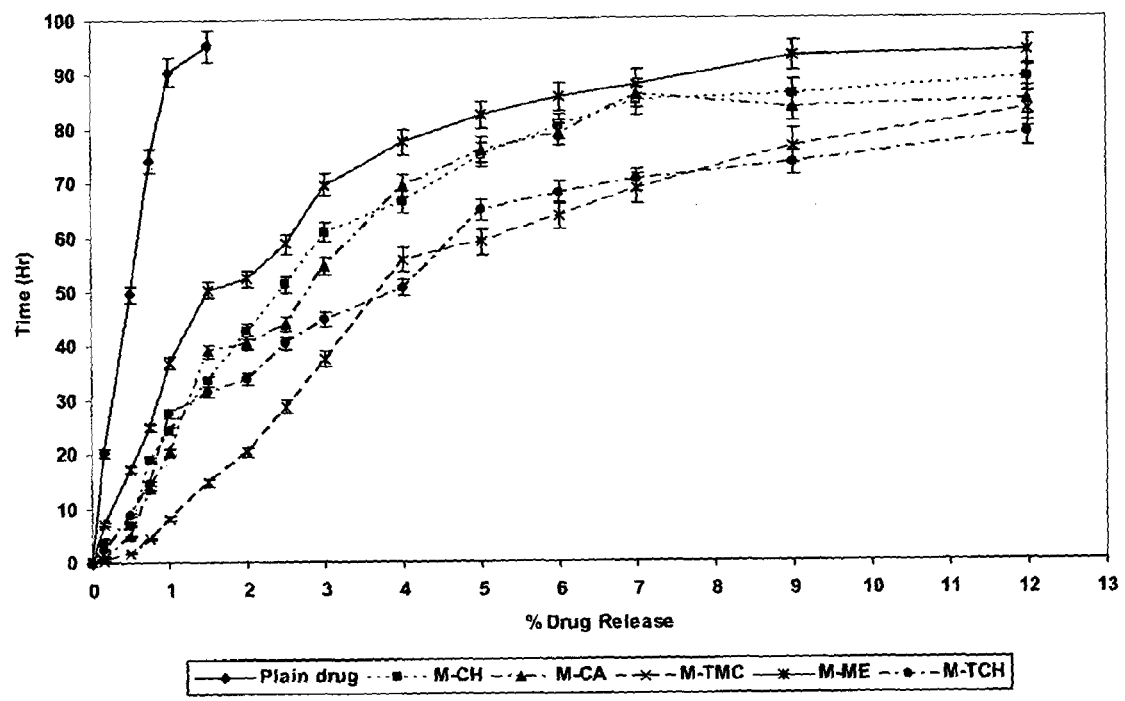

FIG. 3. % In vitro drug release of acyclovir from microspheres formulations. Data are represented as mean±SD (n=3)

Figure 4:
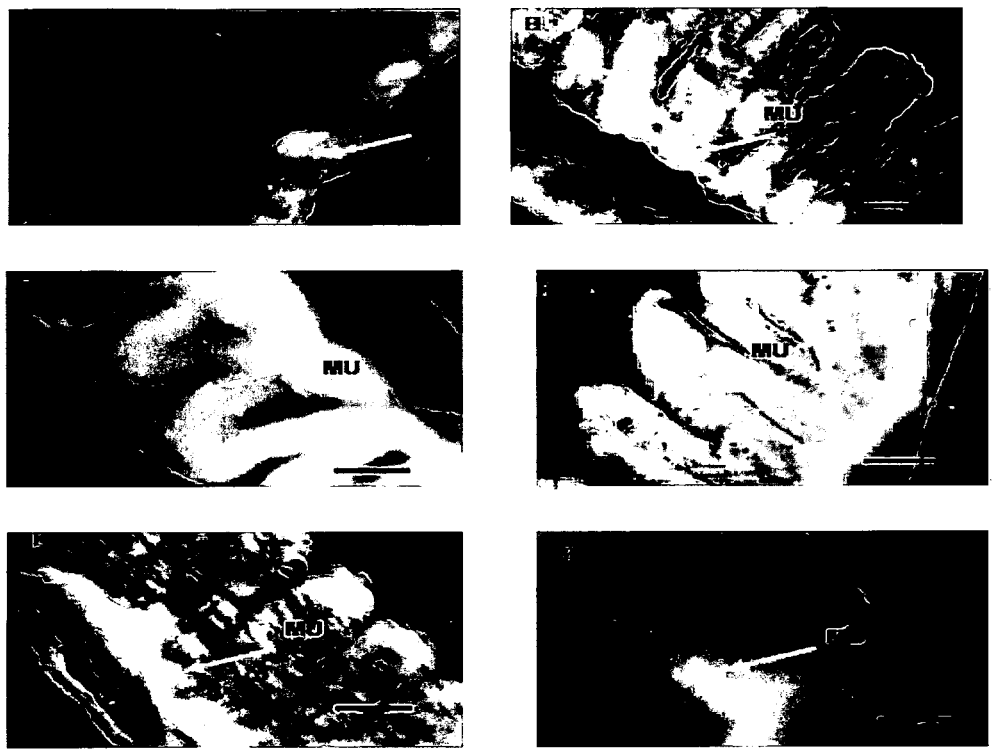

FIG. 4. Penetration of 6-CF (1 ml of 0.3% w/v) as fluorescence probe across the duodenum section of intestinal mucosa after 3 hr administration as solution (A), thiolated chitosan (B), TMC (C), chitosan (D), CARBOPOL® (E) and METHOCEL® K15M (F) microsphere formulation (X 450). Scale bar=250 μm; MU=Mucosal surface; VI=Villi.

Figure 5:
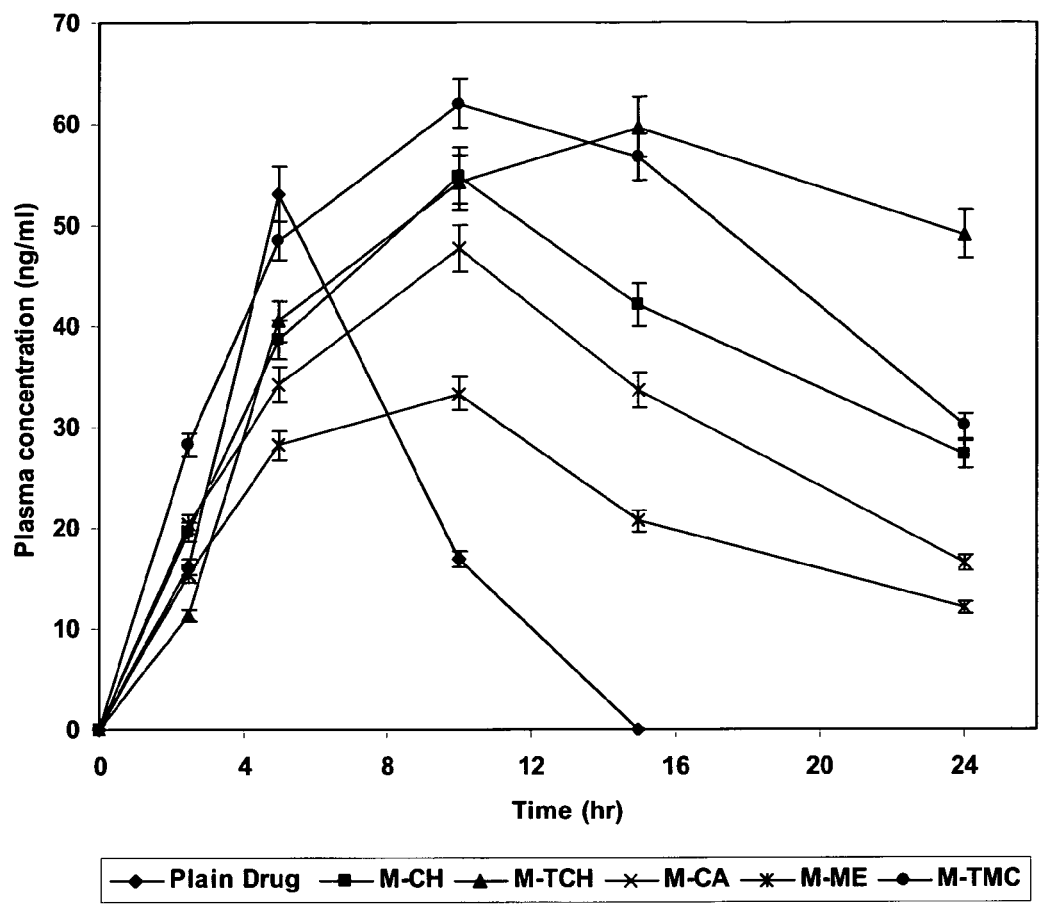

FIG. 5. Plasma concentration of acyclovir after administration as drug solution and microsphere formulations. Data are represents as mean±SD (n=3)

Figure 6:
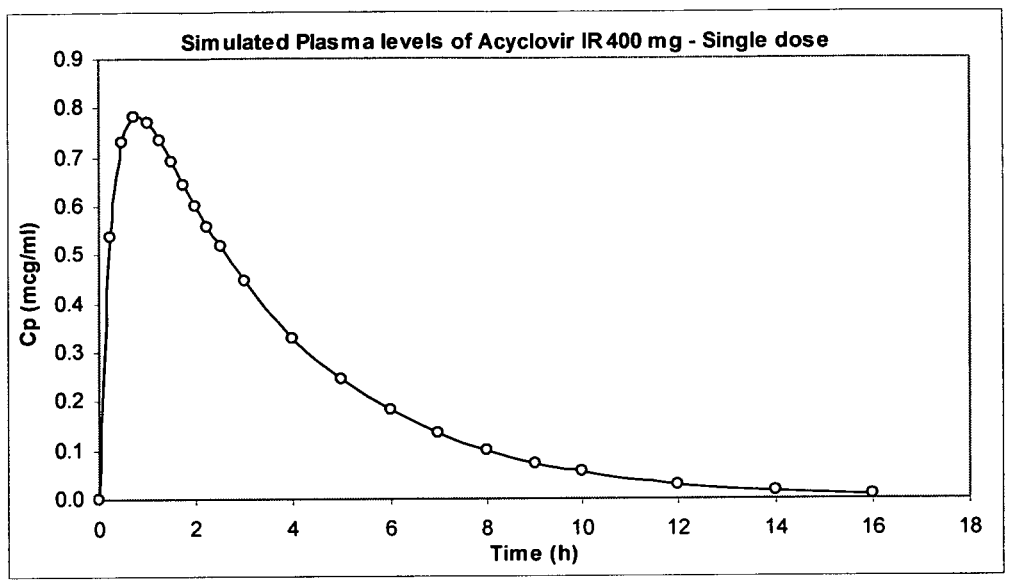

FIG. 6. Showing plasma concentration-time profile of this simulation

Figure 7:
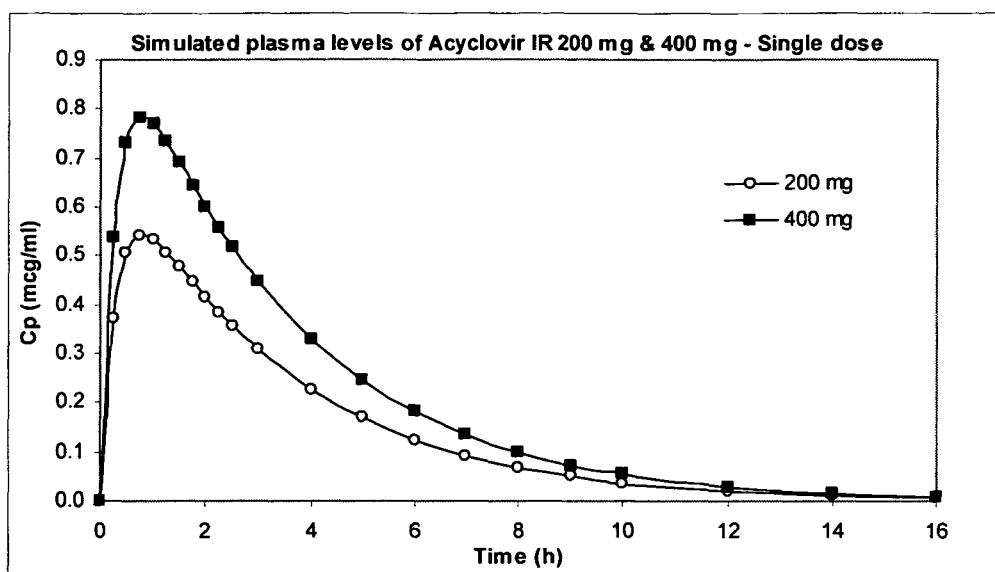

FIG. 7. Showing the comparison of simulated plasma concentration-time profiles of Acyclovir IR 200 mg & 400 mg FIG. 8. Plasma levels of multiple dose administration of Acyclovir IR 200

Figure 9:
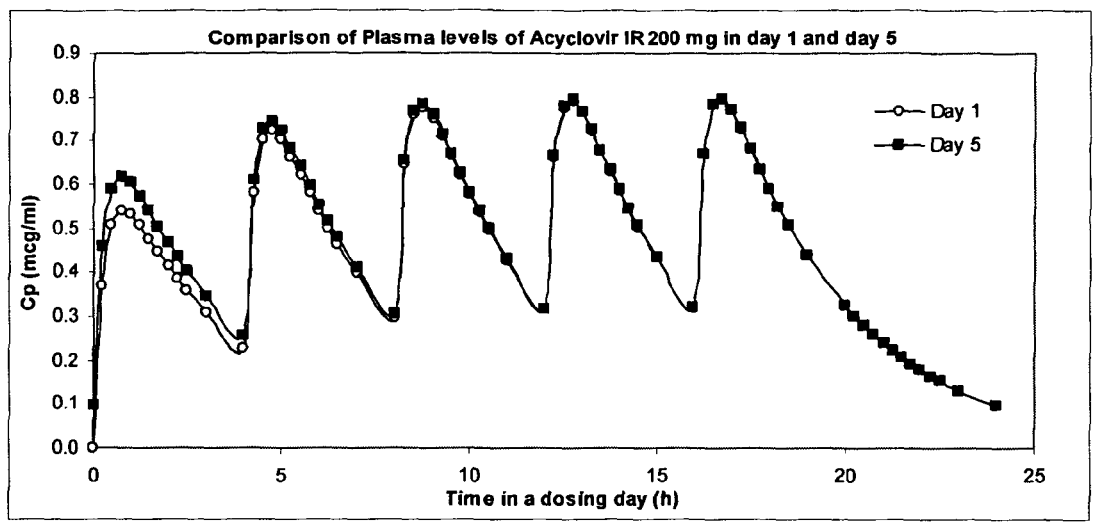

FIG. 9. Shows the comparison of plasma concentrations of Acyclovir IR 200 mg during the dosing day on day 1 and day 5.

Figure 10:
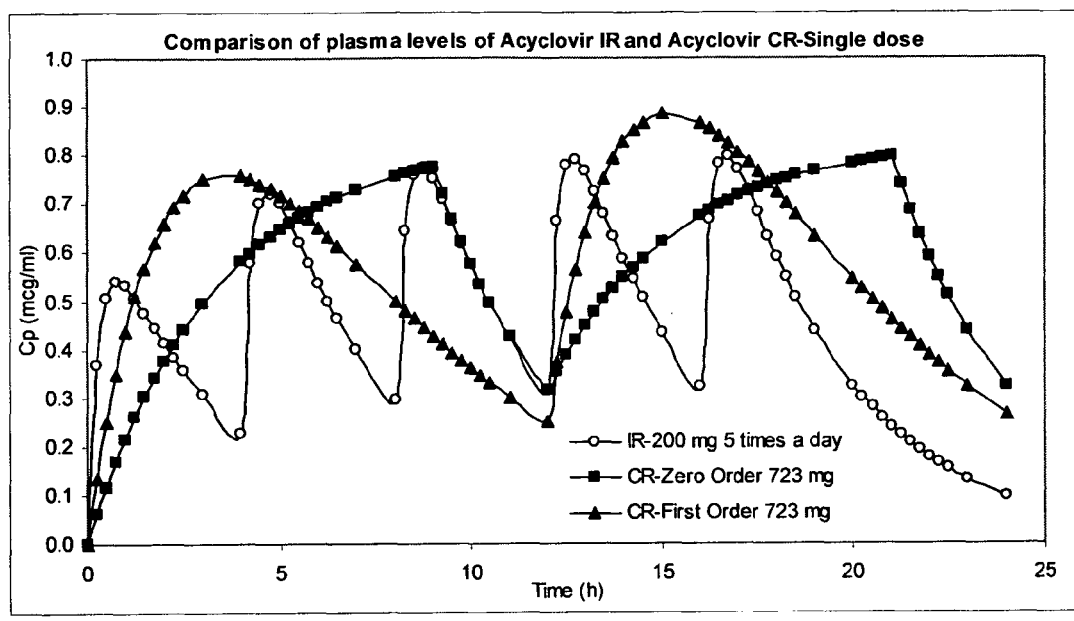

FIG. 10. Comparative plasma concentration profiles of acyclovir immediate release and acyclovir controlled release tablets.

Figure 11:
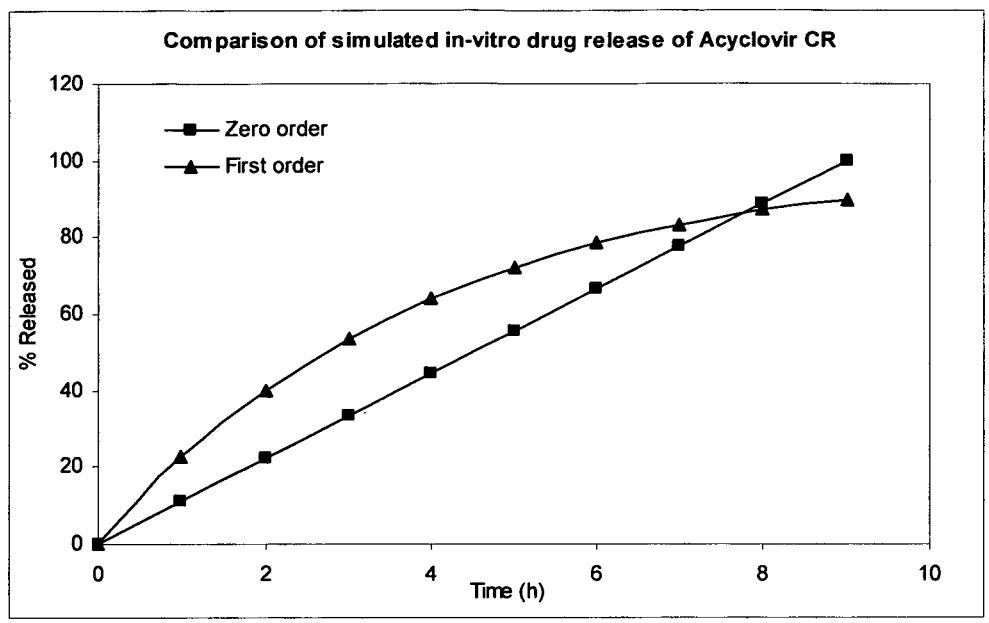

FIG. 11. Predicated in vitro drug release profile of Acyclovir CR formulation

Figure 12:
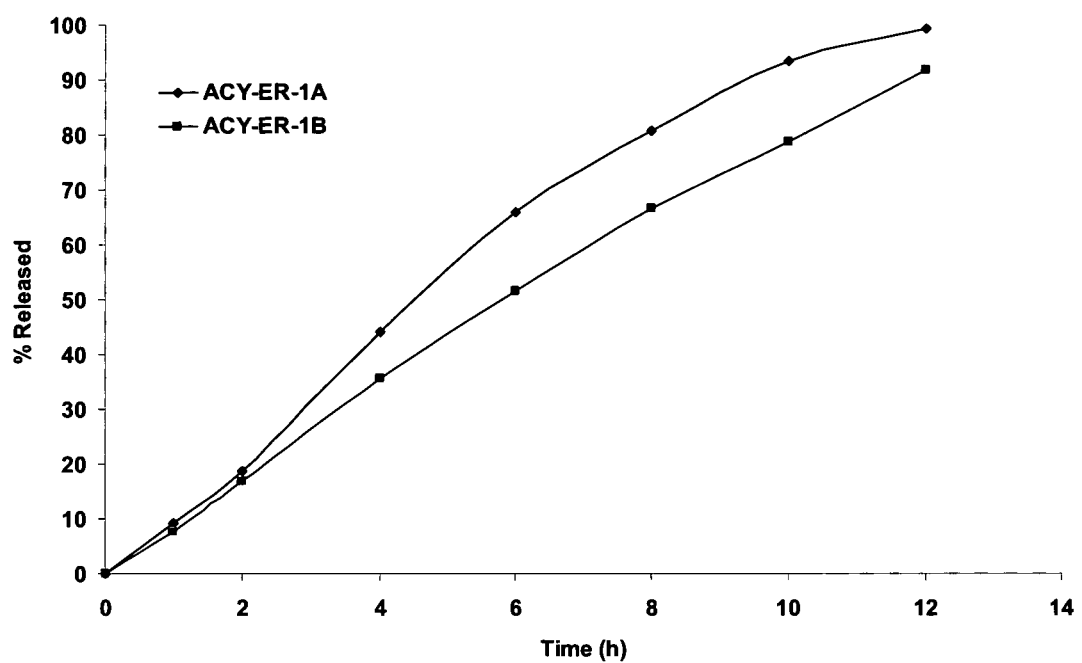

FIG. 12. In vitro drug release profile from gastroretentive tablets prepared using CARBOPOL® 974P as polymer (Batch Acy-ER-1A & Acy-ER-1B).

Figure 13:
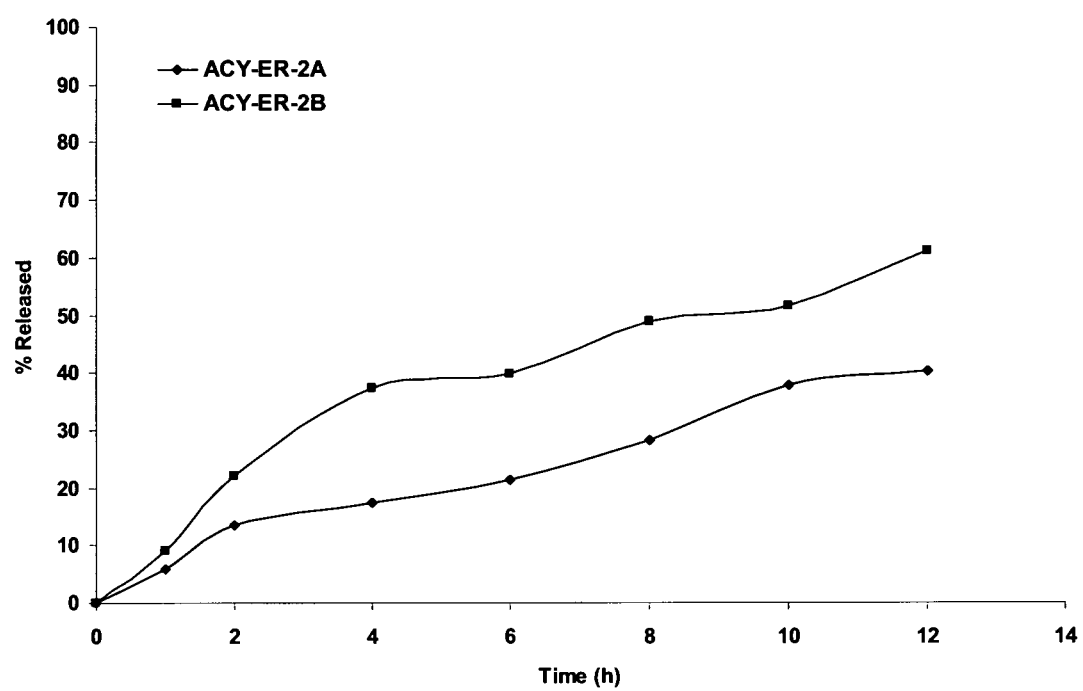

FIG. 13. In vitro drug release profile from gastroretentive tablets prepared using Polyethylene oxide (Batch Acy-ER-2A & 2B).

Figure 14:
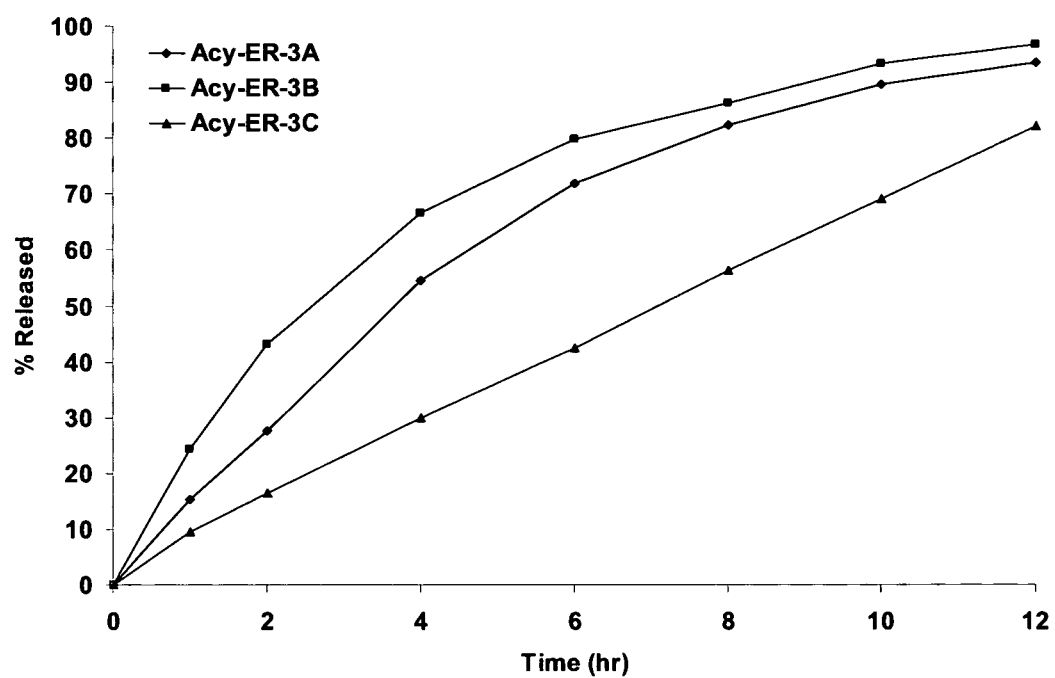

FIG. 14. In vitro drug release profile from gastroretentive tablets prepared using combination of CARBOPOL® 974P and Polyethylene oxide (Batch 3A, 3B & 3C).

Figure 15:
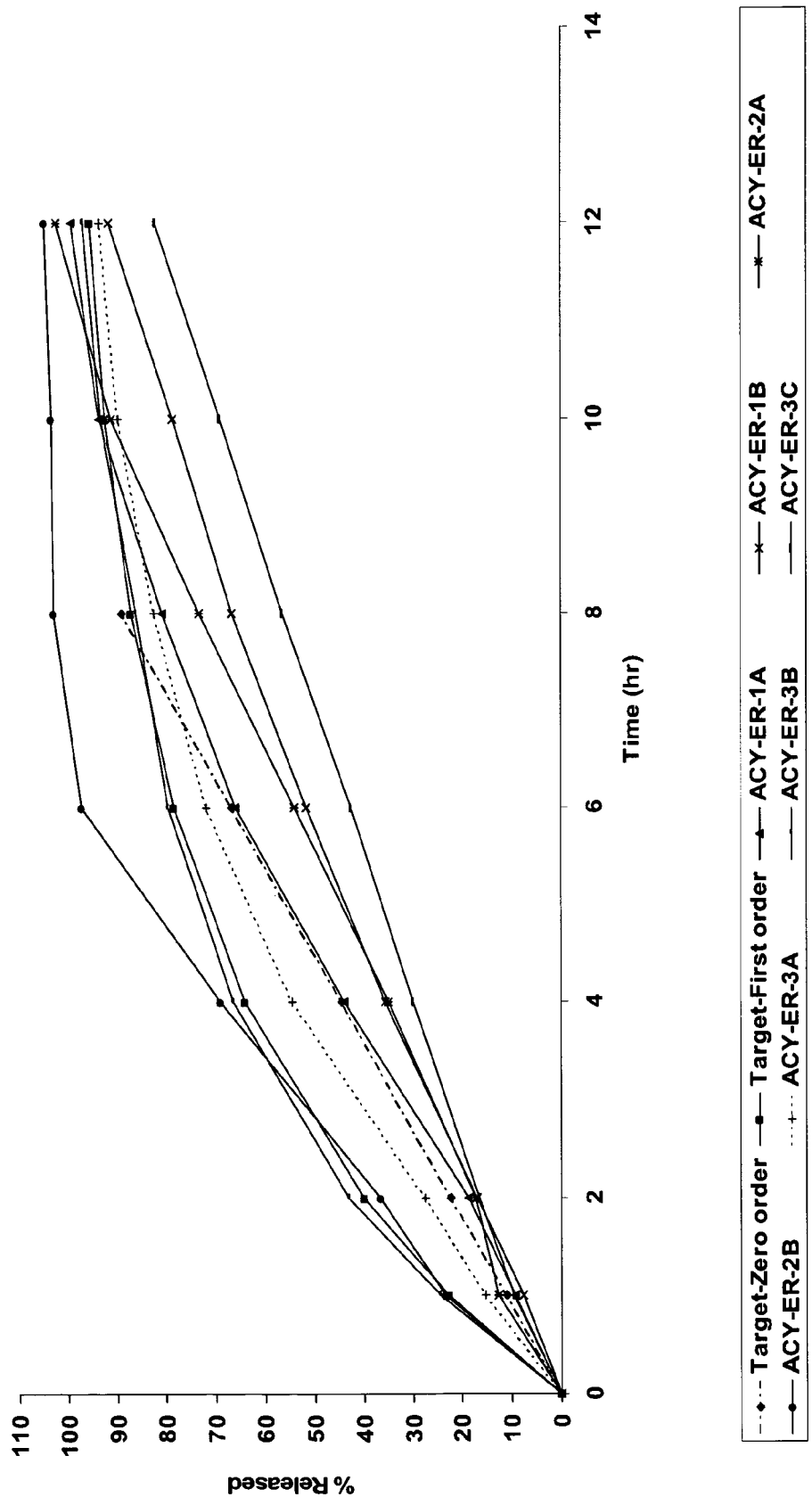

FIG. 15. Comparative In vitro drug release profile from different batches of gastroretentive tablets and target release profile for sustained release acyclovir formulation generated by computer simulation study.

Figure 16:
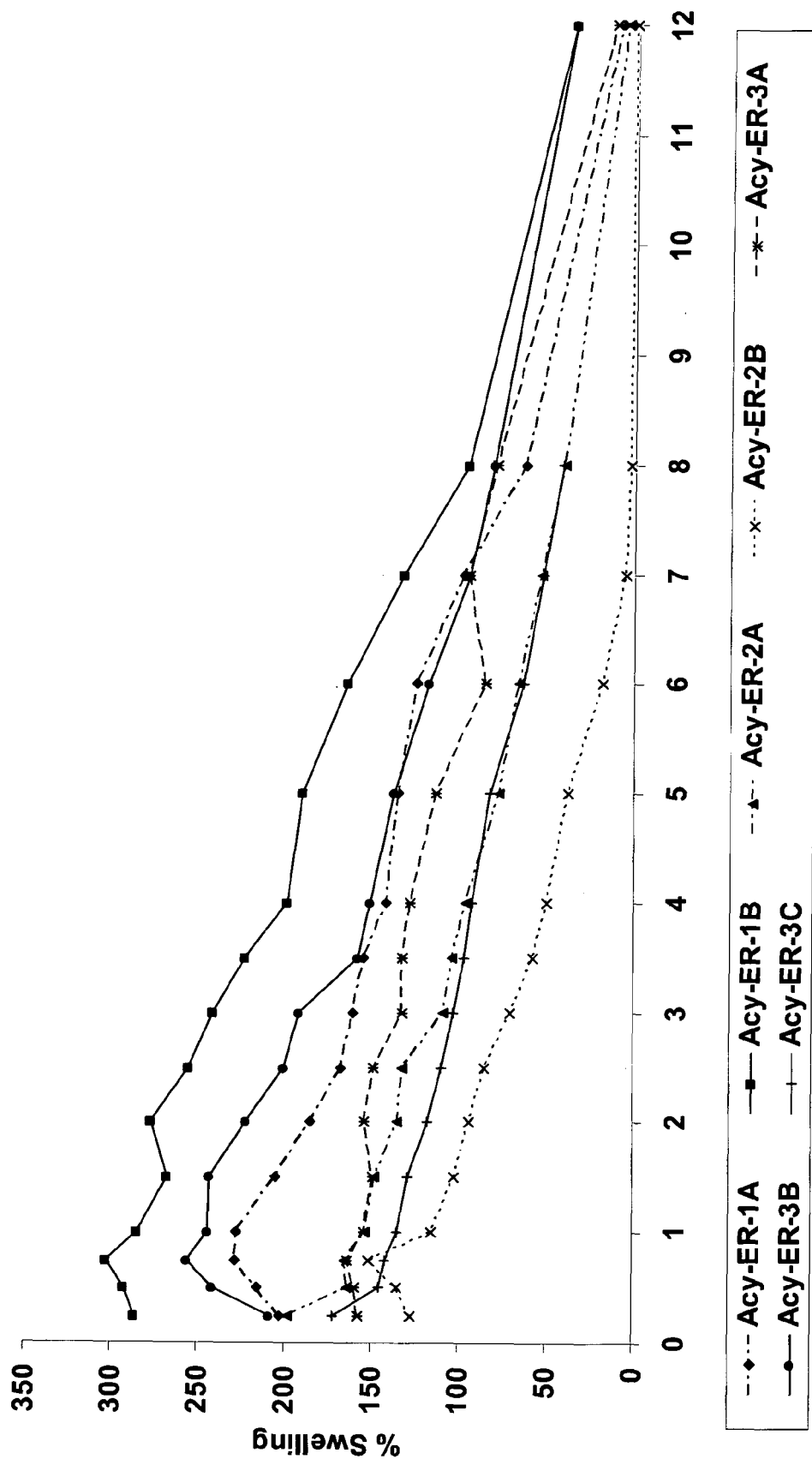

FIG. 16. % Swelling profile from different batches of gastroretentive tablets.

Figure 17:
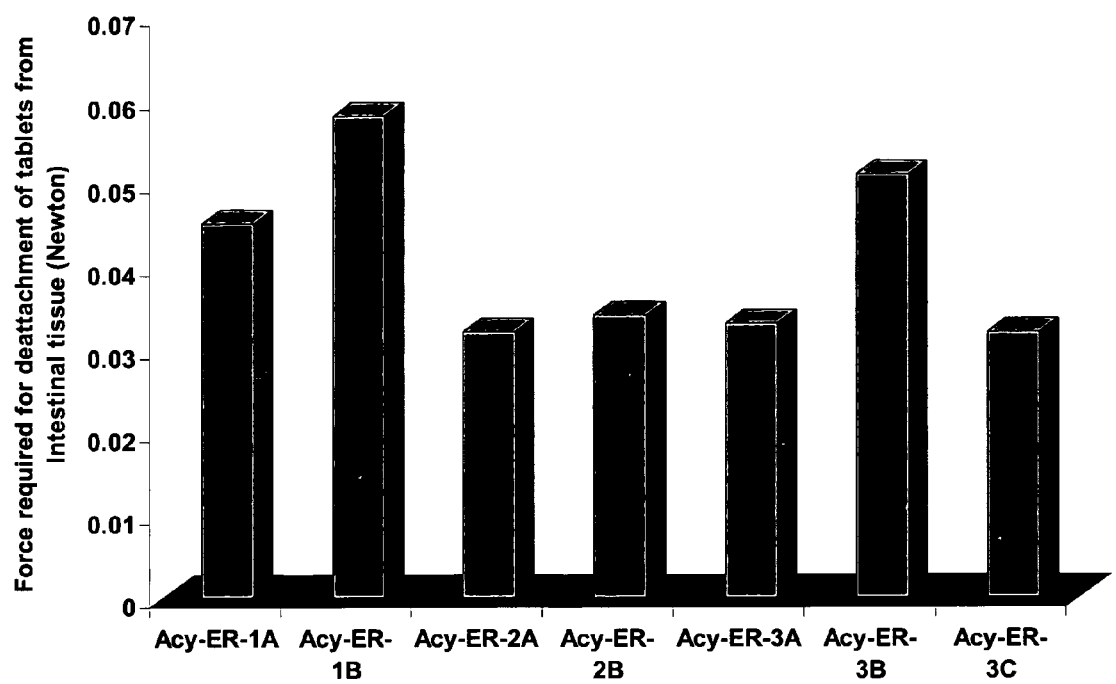

FIG. 17. Mucoadhesive strength measurement of different batches of gastroretentive tablets.

DETAILS OF INVENTION

The polymer/s of present invention include water soluble or water insoluble one/s, further including chitosan and chitosan derivatives exemplified by thiolated chitosan and trimethyl chitosan, CARBOPOL®, HPMC, alginates, pectins, EUDRAGIT®, Hypromellose, polyethylene oxide their combinations and the like. The pharmaceutically acceptable excipient of present invention may be selected from the group of binder, diluent, pH modifier, glidant, lubricant, film formers, anti-adherent, coating agents colorant and the like.

The sustained release delivery system may be in the form of single or multiple units. It can be in the form of tablets, capsules, microsphers, pellets, granules, and like. It can be packed in blister, bottles, sachets and like.

The delivery system may be prepared by the processes well known in the art of formulation development, such as wet granulation, dry granulation, direct compression, blending, extrusion & spheronization, coating and the like.

The sustained release delivery system of present invention may be administered as the dosage required by the patient.

The present invention also deals with pharmacokinetic simulations for a drug, more particularly Acyclovir controlled release (CR) to:

determine the dose and absorption rate required for Acyclovir CR to achieve comparable $C_{max}$ and $C_{min}$ with that of immediate release (IR).

predict the blood levels of Acyclovir CR and compare with that of IR.

simulate in-vitro dissolution profiles from absorption rate constants.

One of the polymer used for sustained release is Chitosan which is a polysaccharide comprising copolymers of glucosamine and N-acetyl glucosamine. It is biodegradable, biocompatible, mucoadhesive polymer and has been used in the formulation of particulate drug delivery system. Chitosan opens the epithelial tight junctions in concentration and pH dependent way. At acidic pH, chitosan is effective in increasing the permeability of certain drugs, but as the pH increases, its effectiveness is decreased.[11] So, to overcome the solubility limitations of chitosan at increased pH values, an N-Trimethyl quartenized chitosan (N-TMC) derivative was synthesized and used for comparison studies. N-TMC has shown potential as an absorption enhancer across intestinal epithelial cells even in neutral environments.[2] The mechanism of drug absorption enhancement by N-TMC is the same as that of chitosan.[12] It opens the tight junctions between the adjacent epithelial cells by means of interaction between the positive charges on the polymer molecules and the anionic components on the surface of epithelial cells.

Another polymer selected in the present study is thiolated chitosan. Thiolated chitosan represents a new promise in the field of mucoadhesive polymers. The higher mucoadhesive properties of thiomers are reported to intensify the contact with gastric mucosa, providing an increased epithelial permeability for many drugs.[13-15] In addition, these polymers are reported to increase the intestinal permeability of drugs that shall be beneficial for increasing the intestinal permeability of acyclovir along with mucoadhesiveness.

In one of the embodiment of this invention drug Acyclovir which is used for the treatment of herpes simplex virus infections, is most widely used drug for infections such as cutaneous herpes, genital herpes, chicken pox, varicella zoster infections and herpes keratitis.[16] Acyclovir is currently marketed as capsules, tablets and suspension for oral administration, intravenous injection and topical ointment. Oral acyclovir is mostly used in dose strength as 200 mg tablets, 5 times a day. In addition, long term administration of acyclovir (six month or longer) is required in immunocompetant patient with relapsing herpes simplex infection.[17] The presently available conventional therapy is associated with a number of drawbacks such as highly variable absorption and low bioavailability (10-20%) and requirement of frequent administration (5 times a day) resulting in poor patient compliance. Furthermore, with increase in dose, there was seen decrease in bioavailability. Moreover, the mean plasma half life of the drug being 2.5 hrs, necessitates repeated administration of high dose of the drug (200 mg five times a day). As a result, most of the drug is excreted in the faeces (50-60%) in unabsorbed form.[18] Acyclovir is soluble in acidic pH and is predominantly absorbed from upper regions of gastro intestinal tract (GIT).[19]

One of the embodiment of the present investigation discloses mucoadhesive microspheres for gastroretentive delivery of a drug. Polysaccharide Chitosan, thiolated chitosan, Trimetyl Chitosan, CARBOPOL® 71 G (High molecular weight polymer of acrylic acid crosslinked with allyl ethers of pentaerythritol) and METHOCEL® K15M and their various combinations were used as mucoadhesive polymers. Microsphere formulations were prepared using emulsion-chemical crosslinking technique and evaluated in vitro, ex-vivo and in-vivo. These microspheres may be administered in dosage forms, including a sachet, as a tablet, through a capsule and the like.

Another embodiment, discloses gastroretentive tablets of acyclovir were prepared from one or more the polymers and excipients for sustained delivery.

In further embodiment of this invention the drug pharmacokinetic simulation was done for Acyclovir CR to:
determine the dose and absorption rate required for Acyclovir CR to achieve comparable $C_{max}$ and $C_{min}$ with that of IR.
predict the blood levels of Acyclovir CR and compare with that of IR.
simulate in-vitro dissolution profiles from absorption rate constants.

In the following are described experiments conducted that serve as non limiting illustrations of how the invention is performed. Any modifications or variations in the parameters including but not limited to polymers used, their combination used, drugs used, chemicals and their concentrations used, various procedures for assaying the drug, simulation of the drug are merely illustrative and any equivalents of them that are obvious to a person skilled in the art and that are capable of achieving the same objective if used in their place shall be considered as included in the content/scope of this specification Materials and Methods
Materials Chitosan (degree of deacetylation 82% and molecular weight 650,000) was obtained as gift sample from Central Fisheries Research Institute, Cochin. METHOCEL® K15M and CARBOPOL® 71G were obtained as gift sample from Colorcon Ltd., Mumbai and Degussa Ltd., Mumbai, respectively. 2-Iminothiolane-HCl, 6-Carboxyfluorescein (6-CF) and Traut's reagent were procured from Sigma-Aldrich Ltd., USA. Ethanol, acetonitrile, methanol and xylene were procured from E. Merck Ltd., Mumbai, India. Thiolated Chitosan and N Trimethyl chitosan (N-TMC) was prepared in the lab according to the method reported by Bernkop-Schnurch et al.[14]

Preparation of Microspheres Formulations

Microspheres formulations using chitosan, N-TMC and thiolated chitosan as polymers were prepared using the emulsification cross linking method (Wang et al.[20]). Emulsification cross linking method was optimized for different process and formulation variables.

A solution of chitosan, (1.0 to 2.0% w/v) was prepared in acetic acid (2% v/v) and aqueous solution of drug (0.1 to 0.5% w/w) was added to their respective solution. This was further added to continuous phase (consisting of light liquid paraffin and heavy liquid paraffin (1:1) containing Span 80 (0.5% w/v) as surfactant) under constant stirring (1200-2000 rpm) using a three blade propeller stirrer to form w/o emulsion. This was followed by addition of gluteraldehyde (0.25 to 1.0 ml, 25% v/v) drop wise at 15, 30, 45 and 60 min, respectively. The stirring was continued for 3.5 hours. The microspheres so obtained were separated by centrifugation and washed with petroleum ether to remove liquid paraffin. The microspheres were suspended in 5% w/v sodium bisulfite solution and stirred for 15 minutes to remove residual gluteraldehyde. Final washing was done with distilled water, microspheres were dried and stored in a vacuum desiccator. Thiolated chitosan and N-Trimethyl chitosan microsphere was prepared using same method using optimized process and formulations variables.

Microspheres of CARBOPOL® 71 G and METHOCEL® K15M were prepared by spray drying techniques as reported by Harikarnpakdee et al.[21] METHOCEL® K15M or CARBOPOL® 71G were dissolved in deionised water. Acyclovir was separately dissolved in distilled water. Colloidal silicon dioxide (Aerosil), maltodextrin and propylene glycol were then mixed with the polymer solution. The solution of each batch was spray dried employing inlet temperature of 120° C. for CARBOPOL® 71G and 130° C. for METHOCEL® K15M, pump setting of 5 ml/min; spray flow rate of 400 nano liter/min.

Fluorescently loaded microspheres were prepared in the same way. For this purpose drug solution was replaced with 0.3% w/v solution of 6-CF and microspheres were prepared using the procedure described above.

Characterization of Microspheres
Morphological Examination

The morphology of microspheres was examined by scanning electron microscopy (SEM, JSM-5310LV scanning microscope Tokyo, Japan). The microspheres were mounted on metal stubs using double-sided tape and coated with a 150° A layer of gold under vacuum using gold coater. Stubs were visualized under scanning electron microscope.

Particle Size Measurement

The particle size of the microspheres was measured using stage micrometer scale. Dry microspheres (5 mg) were suspended in distilled water and ultrasonicated for 5 seconds. A drop of suspension was placed on a clean glass slide and microspheres were counted under stage ocular micrometer. Minimum of 200 microspheres were counted per batch.

Swelling Measurement

The swelling of microspheres was conducted in phosphate buffer pH 6.8. The size of dried microsphere and after incubating in phosphate buffer (pH 6.8) for 0.3, 1.0, 3.0 and 5.0 hr was measured by using microscopic method. The percentage of swelling at different time interval was determined by taking difference between diameter of microspheres at time t ($D_t$) and initial time (t=0 [$D_0$]) as calculated from the following equation $$\text{Swelling \%} = D_t - D_0/D_0 * 100 \quad (1)$$

Production Yield

The production yield (% w/w) was calculated from the ratio of average weight of dried microspheres (W1) recovered from each of three batches to the sum of initial dry weight of starting materials (W2).

Entrapment Efficiency

Acyclovir loaded microspheres (10 mg) of chitosan, N-TMC or thiolated chitosan were digested in HCl (0.01M). CARBOPOL® 71G and METHOCEL® K15M microspheres were dispersed in 0.1M NaOH and 0.05M phosphate buffer (pH 6.8), respectively for overnight with intermittent shaking. The mixture was filtered and filtrate was assayed spectrofluorometrically (Elico Spectrofluorometer, SL-174, Delhi, India) at excitation wavelength of 256 nm and emission wavelength of 374 nm according to the method reported by Darwish et al.[22] The entrapment efficiency was calculated from the ratio of actual amount of the drug present in the formulation to the initial amount of the drug added Mucoadhesion Measurement Study The mucoadhesion property of microsphere formulations was determined according to the method described by Vyas et al.[23] A 5 cm long piece of freshly cut pig intestine was obtained from a local abattoir within 1 hr of killing of animal was further cleaned by washing with isotonic saline solution. An accurate weight of microspheres was placed on the mucosal surface to which was attached a polyethylene plate that was fixed at an angle of 40° relative to the horizontal plane. Phosphate buffer (pH 6.8) warmed at 37±1° C. was flown at a rate of 5 ml/min over the tissue. The time required for detaching all the microspheres from mucosal surface of the pig intestine was recorded by visual inspection.[21]

In Vitro Drug Release Study

In vitro release of acyclovir from microspheres was determined by carrying out dissolution test using USP paddle method at a stirring rate of 50±5 rpm at temperature 37±0.5° C. 900 ml of HCl buffer (pH 1.2) was used as dissolution medium for first hr and phosphate buffered saline (PBS, pH 6.8) was used for next 11 hrs. The dried microspheres were filled in hard gelatin capsules and were placed in dissolution vessels. 5 ml sample was withdrawn at various time intervals and volume of the media was replenished with an equal amount of dissolution media. The samples were then analyzed spectrofluorometrically.

G.I.T Distribution

Rats (Sprague dawley strain), 6 to 8 months old, weighing 200-220 gm were kept on fasting for 16-20 hr before commencement of the experiment. Water was provided ad libitum. The protocols for these investigations were approved by the Institutional Animal ethics committee in accordance with the disciplinary principles and guidelines of CPCSEA. Six groups were employed in the present study with each group containing 15 rats. First group received oral administration of aqueous solution of 6-CF (1 ml of 0.3% w/v). The second, third, fourth, fifth and sixth groups received microsphere of 6-CF prepared from chitosan (M-CH), thiolated chitosan (M-TCH), N-Trimethyl chitosan (N-TMC), CARBOPOL® 71 G or METHOCEL® K15M, respectively. Oral administration of microspheres was accomplished by suspending 20 mg sample of microspheres corresponding to 3.0 mg of 6-CF in 1.0 ml normal saline and force-feeding via a rubber tube under non-anesthetic conditions. The rats were sacrificed after 2, 4, 6, 8 or 10 hr of administration, stomach (section 1) along with entire length of small intestine that was further subdivided into 6 sections (sections 2-7; length of each section 14 cm) were isolated immediately. The stomach and intestinal sections were cut opened to expose the inner mucosal surface. All microspheres located in each part were collected by scratching the mucosa with a spatula. To the collected sample, 10 ml of 0.1 N HCl was added in case of chitosan, thiolated chitosan and N-TMC. The 0.1 N NaOH and phosphate buffer (0.05 M) were added in case of CARBOPOL® 71G and METHOCEL® KI 5M microsphere, respectively. The mixture was mashed using homogenizer to extract 6-CF and kept for 24 hr. After centrifugation at 3000 rpm for 20 min, the supernatant was analyzed fluoremetrically at $\lambda_{exitation}$ 489 nm and $\lambda_{emmission}$ 515 nm for 6-Carboxyfluorescein. The extraction efficiency of 6-CF using this method was found to be approximately 95%. In addition a 2 cm portion of section 2, 3 and 4 was taken out and further processed for fluorescence microscopy.

Fluorescence Microscopy

Fluorescence microscopy was performed to determine the extent of distribution and penetration of microsphere formulations. The excised tissue sections of GIT were blotted with tissue paper. The wiped tissue was fixed in fixative solution (3:1 absolute alcohol: chloroform) for 3 hr. The pieces were first transferred to absolute alcohol for 0.5 hr and then in absolute alcohol and xylene for 1 hr. Wax scrapings were added in this solution till saturation and were kept for 24 hr. Paraffin blocks were made by embedding the tissue in hard paraffin, matured at 62±1.0° C. The sections (5 µm thickness) were cut using microtome (Erma optical works, Japan) and examined under fluorescence microscope (Leica, DMRBE, Bensheim, Germany).

Hemolytic Toxicity Assay

The procedure from literature was followed to perform the hemolytic toxicity studies.[19] Blood from healthy donors was collected and anticogulated with 3% sodium citrate. Erythrocytes were separated from blood plasma by centrifugation (3000×g, 5 min) and suspended in phosphate buffer saline (PBS) of pH 7.4. The RBC suspension (1%) was mixed with distilled water, which was considered as producing 100% hemolysis, and normal saline producing no hemolysis hence acting as blank. 0.5 ml 2% w/v dispersion of microspheres formulations in PBS (pH 7.4) was added to 4.5 ml of normal saline and interacted with 1 ml RBC suspension. Similarly, 0.5 ml of 0.3% w/v solution of acyclovir in PBS were mixed with 4.5 ml of normal saline and interacted with RBC suspension and kept in incubator for 1 hr at 37±1.0° C. After 1 hr, mixture was centrifuged and supernatants were taken and diluted with an equal volume of normal saline and absorbance was taken at 540 nm against supernatant of normal saline diluted similarly as blank. The percentage hemolysis was thus determined for each sample by taking absorbance of water as 100% hemolytic sample.

Pharmacokinetic Study

Rats (Sprague dawley), 6 to 8 months old, weighing 200-220 gm were divided into 6 groups, each consisting of 5 animals. Rats were kept on fasting 12 hours before drug administration and until 24 hours post dosing. Water ad libitum was given throughout the study. The dose selected of acyclovir was 5 mg/kg.[24] First group received oral administration of 0.3% w/v drug solution in PBS (pH 7.4). Second, third, fourth, fifth and sixth group received oral administration of chitosan, thiolated chitosan, trimethyl chitosan, CARBOPOL® or METHOCEL® microspheres, respectively. A 20 mg sample of microsphere corresponding to 3.0 mg of acyclovir were suspended in 1.0 ml saline and administered orally using a rubber tube under non-anesthetic condition. At 2.5, 5, 10, 15 and 24 hrs time intervals, blood was collected from jugular vein in ependorff tubes and centrifuged at 2000 rpm for 10 min (REMI Equipment, Mumbai, India). Supernatant was collected and acetonitrile was added to precipitate the proteins. The precipitated proteins were settled by centrifugation at 2000 rpm for 15 min. The supernatant was collected and filtered through a 0.45 µm filter into volumetric flask and drug concentration was determined by spectrofluorometric assay.

Pharmacokinetic Simulations Performed for Acyclovir Controlled Release

Assumptions considered for simulation performance study are as follows:

1. The product will be indicated for initial and intermittent therapy of genital herpes. These conditions require a dosage of 200 mg every four hours, 5 times daily for 10 days.
2. The product will be a bioadhesive dosage form, which would be designed to be retained in upper part of GIT for a prolonged period of time.
3. The CR formulation will be administered two times a day.
4. Bioavailability of CR formulation is 25% higher than that of IR formulation due to prolonged residence in absorbable areas of GIT.
5. The absorption process is controlled by the release from the dosage form. The intrinsic absorption rate constant of the drug is far higher than the drug release from the dosage form (Ka>>>>>>>>drug release rate) and hence absorption of any amount of drug release from the dosage form is instantaneous.

Simulations Performed

The simulation process involved following steps.
1. As a first step the plasma concentration profiles of Acyclovir/Acyclovir IR tablets were calculated using the pharmacokinetic parameters reported in the literature[16, 18].
2. These parameters were then used to calculate required properties of CR dosage form.
3. Then simulations for CR dosage form were performed using parameters obtained in step 2.

The methodology and results are summarized in table 6-9 and FIG. 6-11.

Platform Used

Computer PIV (1.7 dual processor), 1 GB Ram, 200 GB Hard disk with software Microsoft Excel 2003.

Fabrication of Gastroretentive Acyclovir Tablets

Matrix tablets were prepared by wet granulation method. Acyclovir, polymer and AVICEL® were weighed and sifted together through the sieve #40 ASTM and blended in a polybag for 5 min. Blended material was granulated (what are steps/method of granulation?) using ethanolic solution of PVP-K30. The wet mass was dried in a tray dryer for 30 min at 40° C. and dried materials passed through a sieve #20 ASTM. Granules were blended with magnesium stearate and compressed using 19 mm×9 mm, modified capsules shaped, concave punch. The formulation ingredients of various batches are summarized in Table 9. The hardness of the tablets was kept in the vicinity of 19.6-22.6 kp and thickness was 5.94 and 6.03 mm.

Characterization of Tablets

The properties of the compressed acyclovir gastroretentive tablets, such as hardness, friability, thickness, weight variation, and content uniformity were determined using reported procedure. Briefly, hardness was determined by using Monsanto hardness tester. Friability was determined using Roche friability testing apparatus. Weight variation and uniformity of drug content were performed according to the IP procedures.

In Vitro Drug Release Studies of Acyclovir Gastroretentive Tablets

The in vitro dissolution studies were performed using USP-2 type dissolution apparatus at 50 rpm) and temperature was maintained at 37° C.±0.5° C. Release testing was carried out in 900 ml of different dissolution media: simulated gastric fluid (pH 1.2) and phosphate buffer (pH 6.8). An aliquot (10 mL) was withdrawn at specific time intervals and drug content was determined by UV-visible spectrophotometer) at 255 nm. It was made clear that none of the ingredients used in the tablet formulations interfered with the assay.

Water Uptake Kinetics

Water uptake studies were performed by equilibrium weight gain method using USP type I dissolution test apparatus. The tablets were accurately weighed and placed in a dissolution basket. The basket was immersed in a dissolution vessel containing 900 ml 0.1 N HCl (pH1.2) maintained at 37±0.5° C.; speed of rotation was 50 rpm. At regular intervals, the basket-matrix system was removed from the dissolution vessel, blotted with tissue paper to remove excess water, and reweighed. The percentage water uptake (i.e., the degree of swelling due to absorbed medium) was calculated using following equation.

$$\% \text{ Water Uptake} = W_t/W_0 \times 100 \qquad (2)$$

Where $W_o$ and $W_t$ are weights of dry and swelled tablet at time t, respectively.

Matrix Erosion Studies

Matrix erosion studies were performed by a method reported by Ebube et al.[25] USP type I dissolution test apparatus was used for this purpose. The dry tablets were weighed, placed in dissolution basket containing 900 ml of 0.1 N HCl (pH 1.2) maintained at 37±0.5° C. and the basket was rotated at 50 rpm. At regular intervals, the whole basket-matrix assembly was removed from the dissolution vessels and dried to a constant weight in a hot-air oven at 50° C. The matrix erosion (E) at time, t, was estimated from Eq. 3.

$$\text{Matrix erosion } \% = W_{dt}/W_0 \times 100 \qquad (3)$$

Wdt and Wo are weights of dried tablet and initial weight of dry tablet at time t respectively.

Mucoadhesive Measurement Study of Acyclovir Gastroretentive Tablets

Mucoadhesive strength of acyclovir gastroretentive tablets were determined by detachment force measurement method using pig intestine. Immediately after slaughter, different parts of intestine were removed and transported to Tyrode solution kept at 4° C. The composition of tyrode Tyrode solution (g/L) is NaCl, 6; KCl, 0.2; CaCl2 2H2O, 0.134; NaHCO3, 1.0; sodium hydrogen phosphate, 0.05; glucose-H2O, 1.0. During the experiment, the solution was aerated with pure oxygen and kept at 37° C. The intestinal tissue was fixed on glass plate of receptor compartment. The tablet was placed over intestinal tissue and on the other end of the glass rod a pan was attached in which a beaker was placed. After keeping the preparation for 30 min, the water was added with a burette dropwise to the beaker. The force needed to detach the tablet was measured using a modified prescription balance. The force was used as a parameter for adherence. The force F in newtons was calculated by the equation $$F = 0.00981 W/2 \qquad (4)$$

Where W is the amount of water in the beaker in grams.

Statistical Analysis

Data are expressed as the mean±standard deviation (SD) of the mean. Statistical analysis was carried out employing the student's t test using the Graph-pad PRISM software (Version 2.01, San Diego, Calif.). A value of $p<0.05$ was considered statistically significant.

Results

Preparation and In Vitro Characterization

Table 1 shows the composition of different microsphere formulations prepared using chitosan, thiolated chitosan and trimethyl chitosan as polymers and results were compared with microsphere prepared with widely used mucoadhesive polymers CARBOPOL® 71G and METHOCEL® K15M.

Twenty different types of microsphere formulations were prepared using four different formulations and process variables. Initially, chitosan microspheres were prepared using different drug concentrations (batch CH-A1 to CH-A5 containing 0.1 to 0.5% w/v acyclovir), different polymer concentrations (batch CH-B1 to CH-B5 containing 1.0 to 5.0% chitosan), different volume of cross linker (batch CH-C1 to CH-C5 containing 0.25 to 1.0 ml glutaraldehyde) and different speed of stirring (batch CH-D1 to CH-D5 prepared at 1200 to 2000 rpm). Optimization of each variable was carried out on the basis of their characterization in terms of surface morphology, particle size, entrapment efficiency and in-vitro drug release and data is summarized in Table 2.

Batch CH-D5 (acyclovir con. 0.3% w/w, chitosan, 2% w/v, volume of cross linker, 1.0 ml and speed of stirring at 2000 rpm) was selected as optimum batch because it exhibited high entrapment efficiency (88.0±4.1%), possessed perfectly spherical shape and sustained the drug release (71.1±2.8% drug release at 11 hr). Two batches of microsphere formulation M-TMC and M-TCH using all the above optimized values was prepared using N-Trimethyl chitosan chloride and thiolated chitosan instead of chitosan as polymer.

FIG. 1 (A-E) depict the photomicrographs of microspheres prepared using chitosan, N-TMC, thiolated chitosan, CARBOPOL® 71G and METHOCEL® K15M polymers. All microsphere formulations were spherical in shape and possessed smooth surface as visualized under SEM. The size of different microspheres formulation was found to range from 11.2±0.4 to 21.3±1.0 μm (Table 2). The particle size was dependent mainly on the concentration of the polymer and stirring speed. Table 2 shows the effect of stirring rate on the particle size of microspheres. The results showed that increasing the stirring speed from 1200 to 2000 rpm decreased the particle size from 21.3±0.9 μm to 12.5±0.3 μm. This can be attributed to the greater energy generated at higher stirring speed, which was able to efficiently disperse the bigger droplets to smaller ones having less particle size. Increase in the concentration of polymer from 1 to 3% w/v produced a significant increase ($p<0.05$) in the particle size. However, thereafter further increase in polymer concentration (from 3 to 5% w/v) didn't significantly ($p<0.05$) influence the particle size. When the chitosan concentration was increased from 1 to 3%, the viscosity of chitosan solution increased and bigger droplets of the internal phase during emulsification step were produced. This increase is high enough to result in difficult dispersion and subdivision of droplets thus, resulting in large size of microspheres. It was observed that the volume of glutaraldehyde (cross-linker solution) did not have a significant influence ($P<0.05$) on the particle size and entrapment efficiency of the microspheres. On the other hand, stirring speed did significantly effect ($P<0.05$) the particle size of microspheres. An increase in the stirring speed from 1200 to 2000 rpm significantly decreased ($p<0.05$) the particle size. The geometric mean diameter decreased from 21.3±0.9 to 12.5±0.3 μm with an increase in the stirring speed. Microspheres prepared at higher stirring speed were perfectly spherical compared to lower stirring speed, which resulted in the formation of clumps. Microspheres became more discrete with increase in the stirring speed from 1200 to 2000 rpm (Table 2).

Entrapment efficiency of different microsphere formulations was found 55±1.8 to 91.6±3.1% (Table 2). Entrapment efficiency was found to be mainly dependent on the concentration of polymer used. Other formulation and process variable didn't show any significant ($p<0.05$) effect. The result of entrapment efficiency measurement was well correlated with the previous report of Thanoo et al.[26]

The production yield of optimized microsphere formulations was found to be 74.5±3.5, 72.4±2.8, 76.3±3.8, 69.4±4.1 and 54.1±3.0, respectively, for chitosan, N-TMC, thiolated chitosan, CARBOPOL® 71G and METHOCEL® K15M polymers. The entrapment efficiency (% w/w) of acyclovir in optimum batch of microspheres prepared from chitosan, N-TMC, thiolated chitosan, CARBOPOL® 71G or METHOCEL® K15M was found to be 88.0±2.6, 91.3±4.5 86.8±3.1, 91.4±4.2 and 77.3±4.2, respectively (Table 3).

Mucoadhesive Measurement

Table 3 summarized the results of mucoadhesive measurement of different microspheres formulation in pig intestine. The adhesion time of microspheres followed the rank order of thiolated chitosan (8.0±0.8 hr)>N-TMC (4.9±0.6) chitosan (3.1±0.4 hr)>CARBOPOL® 71G (1.1±0.2) >METHOCEL® K15M (0.2±0.1 hr). Without getting bound to any theory we have following understanding on various observations in this inventions. Comparatively poor mucoadhesion of METHOCEL® microspheres could be attributed to its non-ionic property. On the contrary, strong electrostatic attraction seems to have contributed to good mucoadhesion between mucin and CARBOPOL® 71G or chitosan. Numerous hydrophilic functional groups such as carboxyl groups in chitosan molecules have an ability to form hydrogen bonds with the mucus molecules. This interaction is reported to be responsible for mucoadhesive property of this polymer.[21] N-TMC microsphere has significantly higher mucoadhesion in comparison to chitosan microsphere due to ionic nature of N-TMC bearing the positive charge that will form a strong bond with —SH group of mucin resulting in strong mucoadhesion. CARBOPOL® microspheres possessed negative charge, which in presence of investigating medium PBS buffer (pH 6.8) could have been repelled by the negatively charged mucus leading to poor mucoadhesion.

The excellent mucoadhesion was observed in thiolated chitosan microspheres may be due to presence of thiol groups, which are known to enhance the mucoadhesive property of chitosan because of formation of strong covalent bonds (disulfide bonds) with mucin. The formation of disulfide bonds between the thiomer and the mucus gel layer takes place either through thiol/disulfide exchange reaction or via a simple oxidation process of thiol groups.[27] However, other polymers like chitosan or CARBOPOL® form non-covalent bonds like hydrogen bonds, van der Waal's forces or ionic interactions thereby resulting in weak mucoadhesion.

Swelling Study

Figure 2:
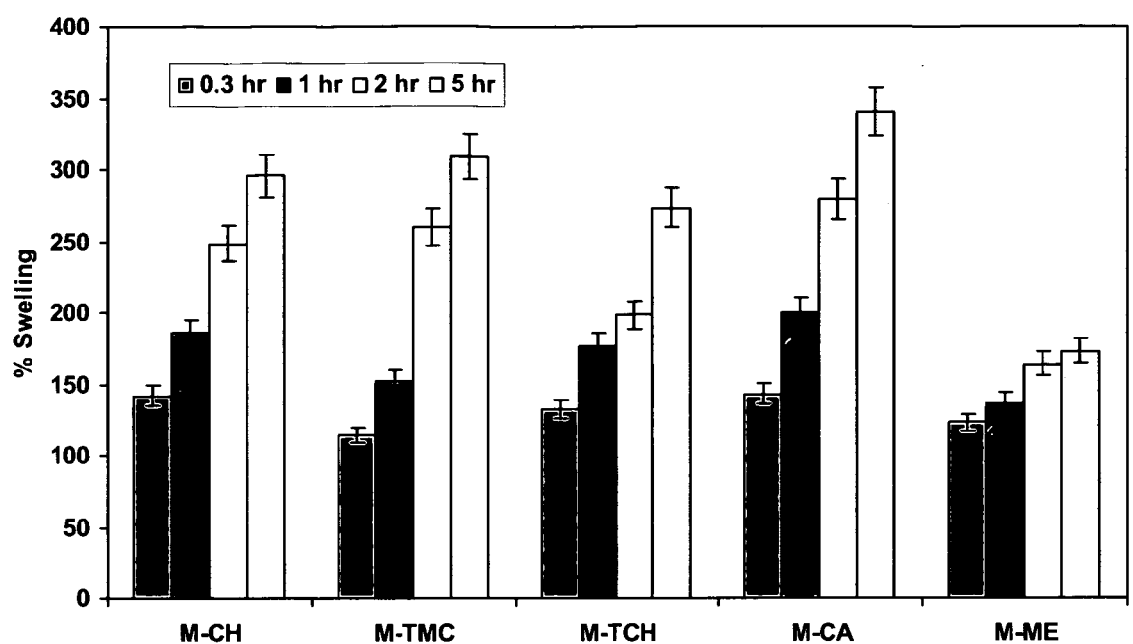

FIG. 2 shows the percentage swelling of different microsphere formulations at different time intervals. The results revealed that all microsphere formulations swelled rapidly when immersed in phosphate buffer (pH 6.8). It is reported that adhesive properties and cohesiveness of mucoadhesive polymers are generally affected by their swelling behavior.[28] Mucoadhesive microspheres are supposed to take up water from underlying mucosal tissue by absorbing, swelling, and capillary effects, leading to considerable stronger adhesion.[29] % Swelling of different microsphere formulation was found to follow the rank order 248.3±18, 260.1±20, 198.2±15, 279.1±26 and 164±15%, respectively, after 2 hr for microsphere prepared from chitosan, N-TMC, thiolated chitosan, CARBOPOL® 71G and METHOCEL® K15M. After 5 hr of incubation % swelling was observed to be 295.5±28, 309.2±24, 273.2±24, 340.7±30 or 173.1±15%, respectively. Chitosan and METHOCEL® K15M microspheres showed significantly less (p<0.05) swelling as comparison to thiolated chitosan, N-TMC or CARBOPOL® 71G microsphere. It was observed that N-TMC and thiolated chitosan microspheres swell slowly and produced higher mucoadhesive strength. This is perhaps because slow swelling avoids the formation of over hydrated structure that looses its mucoadhesive properties before reaching the target.[30] On the other hand, highest swelling observed in microspheres of CARBOPOL® 71G could be due to its high ionization at pH 6.8, which is capable of absorbing high amount of water.[31]

In Vitro Drug Release

FIG. 3 shows the release of acyclovir from various mucoadhesive microspheres. Drug powder enclosed in hard gelatin capsules was completely released (95.3±4.1%) with in 1 hr. The time taken to release 75% of acyclovir ($t_{75}$) from chitosan, N-TMC, thiolated chitosan, METHOCEL® K15M or CARBOPOL® 71G microspheres was 5.0±0.4, 8.0±0.6, 9.5±0.7, 4.0±0.3 and 5.5±0.6 hr, respectively. The significantly higher time required (p<0.05) by the thiolated chitosan microspheres to release acyclovir may be due to its better stability in acidic medium, which contributed significantly less amount of drug release during initial 1 hr of dissolution (29.3±1.1% and 20.5±0.5% drug released from chitosan or thiolated chitosan microsphere during 1 hr). This initial higher release of acyclovir from chitosan microspheres may be attributed to the higher solubility of chitosan in acidic medium. Chitosan is soluble in acidic medium but crosslinking with glutaraldehyde through its amino group stabilized the microspheres matrix and provide the sustained release.[26] Significantly lesser drug release from thiolated chitosan microspheres is due to the presence of disulphide bonds in microsphere matrix further stabilized the structure along with glutaraldehyde as cross linking agent. Higher amount of drug released from METHOCEL® K15M microspheres could be assigned to its linear structure and low viscosity at pH. It was surprising that whereas the microspheres of acrylamide grafted dextran and CS released 20 to 40% acyclovir in first hour itself, microspheres from trimethyl chitosan released only about 7% chitosan in the first hour leading to most uniform drug release profile over a period of 12 hours ultimately leading to 80% release in 12 hours, while microspheres from other investigated compositions released drug ranging from about 20% (for microspheres of CARBOPOL®) to about 35% (for microspheres of METHOCEL®) in first hour.

The release rate from microsphere depend on many factors like concentration of polymer used, method of preparation, amount of cross linker used and amount of drug used, dissolution conditions etc., For the characterization of the release kinetics the in vitro drug release data was fitted to zero order, first order and Higuchi equation $$M_t/M_f = Kt^n$$

Where, $M_t$ is the amount of drug release at time t; $M_f$ is the amount of drug release after infinite time; K is the release rate constant; n is the diffusional exponent indicative of the operating release mechanism.

Quantitative GIT Distribution

Table 4 shows the time course of distribution of mucoadhesive microspheres loaded with 6-CF in the GI tract, including the stomach (Section 1) and small intestine (Section 2-7) after oral administration has been determined. 6-CF was selected as fluorescence marker because of its hydrophilic nature, higher extraction efficiency (>95%) and lower detection limit (1.0 ng/ml). Following oral administration, more than 30% 6-CF solution was recovered from stomach, but less than 10% was located after 4 hr. Maximum amount of 6-CF was transferred to the lower part of intestine after 8 hrs of its administration in rats. The reason for poor retention of 6-CF at absorption site is its soluble nature and its very little affinity to GIT tissue. On the other hand oral administration of 6-CF loaded thiolated chitosan microspheres revealed a different GI distribution pattern. After 2 hr, 22.3±3.1% formulation was recovered from stomach (Section 1) and after 4 hr, nearly 41.6±2.9% was recovered from Section 2, 3 and 4 (duodenum and jejunum portion of intestine). Further, after 10 hr of administration, 26±2.1% formulation was recovered from Section 2, 3 and 4. The significantly higher quantity of acyclovir recovered (p<0.05) from sections 2, 3 and 4 of GIT suggest gastroretentive characteristic of thiolated chitosan microsphere formulation. In comparison chitosan, CARBOPOL® 71G and METHOCEL® K15 microspheres showed 33.5±4.2, 17±2.8 and 9.6±1.4% recovery from section 2, 3 and 4 of GIT after 4 hr of oral administration and 12.9±1.2, 2.5±0.3, 0% recovery after 10 hr of administration. The 2-fold higher GI retention of thiolated microspheres in comparison to chitosan, CARBOPOL® 71G and METHOCEL® K15M microsphere formulation may be attributed to the better mucoadhesive properties of thiolated chitosan in pH 5-6 that is the pH of duodenum and jejunum region of intestine.[32] The main problem with the conventional therapy of acyclovir is its poor retention in duodenum and jejunum region resulting in very poor absorption of drug and nearly more than half of the drug is recovered in the faeces in unchanged form.

Qualitative GIT Distribution Study

Gastroretentive characteristic and permeation enhancement effects of microsphere formulations was determined by carrying out by determining the extent of penetration across the duodenum and jejunum section (Section 2, 3 and 4) of fluorescence marker (6-CF) loaded microspheres formulation. FIG. 4 (A-F) shows the photomicrograph of rat intestine after treatment with 6-CF solution (5A), thiolated chitosan (5B), N-TMC (5C), chitosan (5D), CARBOPOL® 71G (5E) or METHOCEL® K15M (5F) microspheres. The fluorescence photomicrographs revealed better qualitative uptake and localization of fluorescence marker loaded mucoadhesive microsphere in duodenum and jejunum as compared to its solution. Oral administration of 6-CF loaded thiolated chitosan and N-TMC microsphere showed higher fluorescence intensity accompanied with deep penetration of marker in intestinal tissue (FIG. 5B, 5C). This indicates higher mucoadhesiveness and penetration enhancement effect of thiolated chitosan and N-TMC microsphere formulation. Thiolated chitosan and N-TMC is reported to open the tight junction of intestinal epithelium by interacting with intestinal protein this is responsible for its penetration enhancing effect.[32] Acyclovir is a Class III drug. Its low permeability is the rate-limiting factor influencing its oral absorption. Hence, these results indicate that the penetration enhancement effect of thiolated chitosan microspheres could be beneficial in facilitating the oral absorption of acyclovir.

Hemolytic Toxicity Assay

Hemolytic assay is a simple method widely used to study polymer-membrane interaction. It gives a quantitative measure of hemoglobin release. Table 5 compares the results of % hemolysis of different microspheres formulations of acyclovir. Thiolated chitosan, N-TMC, chitosan, CARBOPOL® 71 G and METHOCEL® K15 M microspheres showed 13.1±1.2, 27.2±1.8, 20.1±2.0, 26.2±3.4 and 22.0±2.8% hemolysis, respectively after 1 hr of incubation. Thiolated chitosan microsphere displayed a lower membrane damaging effect causing a significantly lower hemoglobin release than chitosan microsphere. In the case of the thiolated chitosan microspheres the lower membrane-damaging effect in comparison to the chitosan microsphere might be explained by the formation of intra- as well as inter-molecular disulfide bonds, thus leading to a higher rigidness of the microsphere matrix. Rigid molecules have more difficulties to attach to the cellular membrane than flexible molecules and showed toxicity.[33] These findings are in good agreement with previous studies of Guggi et al.[34] asserting that chitosan-TBA and glucosamine-TBA conjugates have a significant less toxic effect on red blood cells in comparison to unmodified chitosan and glucosamine Pharmacokinetic Study FIG. 5 shows the plasma concentration profile of acyclovir after oral administration in the form of solution and microspheres. Thiolated chitosan microspheres showed superiority over the other formulations in plasma concentration at 24 hours. Nearly 4.0 times higher $AUC_{0-24}$ value of acyclovir for these microspheres (1090.7±51 ng·hour/ml) as compared to drug solution (281.7±28 ng·hour/ml) was observed. For Trimethyl chotosan microspheres, however, this value that was still higher i.e. 1335.5, rise in plasma concentration was earlier and higher, achieved highest plasma concentration at 10 and 12 hours which lowered than Thiolated chitosan at 24 hours. Thus, for a 12 hours dosing, Trimethyl Chotsan may be superior than Thiolated Chitosan, although on account of significantly low haemolytic activity, Thiolated chitosan may be considered preferable over Trimetyl chitosans and best amongst all the microsphere compositions tested here. Gastroretentive characteristic of microsphere formulations was further supported by significantly higher (p<0.05) relative bioavailability 387% for M-TCH) as compared to drug solution. In addition, thiolated chitosan microspheres showed the ability to maintain the acyclovir plasma concentration through 24 hr as compared to the drug solution that could maintain this level of drug only for 5 hr. These results confirmed the sustained release potential of mucoadhesive microspheres of acyclovir prepared from thiolated chitosan. Hence, the overall better pharmacokinetic performance of thiolated chitosan microsphere in comparison to drug solution is due to (1) increased residence time within upper GI tract as evident by GI distribution study (2) an intensified contact between the intestinal mucosa and microspheres as evident by mucoadhesion study (3) increased drug concentration at site of absorption as evident by in vitro drug release study and (4) facilitated drug permeation through mucosa as evident by fluorescence microscopy study.

Plasma Concentration Profiles of Acyclovir IR 400 mg—Single Dose

Three parameters, time for maximum plasma concentration ($t_{max}$), elimination half life ($t_{1/2}$), and area under plasma concentration profile (AUC) were collected from literature[16, 18, 35, 36]. Other pharmacokinetic parameters were calculated from these values and provided in the table 6.

A simulation was performed to calculate the plasma concentrations during the course of single dose by using the parameters described in the table 7. The $C_{max}$ was 0.78 mcg/mL. The FIG. 6-11 shows the plasma concentration-time profile of this simulation.

Plasma Concentration Profiles of Acyclovir IR 200 mg—Single Dose

Plasma concentrations of Acyclovir IR 200 mg were calculated from the simulated blood levels of Acyclovir IR 400 mg by extrapolation. The pharmacokinetics of Acyclovir is less than dose proportional (non-linear pharmacokinetics). Hence, the plasma concentrations of 400 mg dose were not linearly extrapolated, but a ratio of 0.69 was used (200 mg:400 mg)[1]. The FIG. 7 shows the comparison of simulated plasma concentration-time profiles of Acyclovir IR 200 mg & 400 mg.

Plasma Concentration Profiles of Acyclovir IR 200 mg—Multiple Dose

Figure 8:
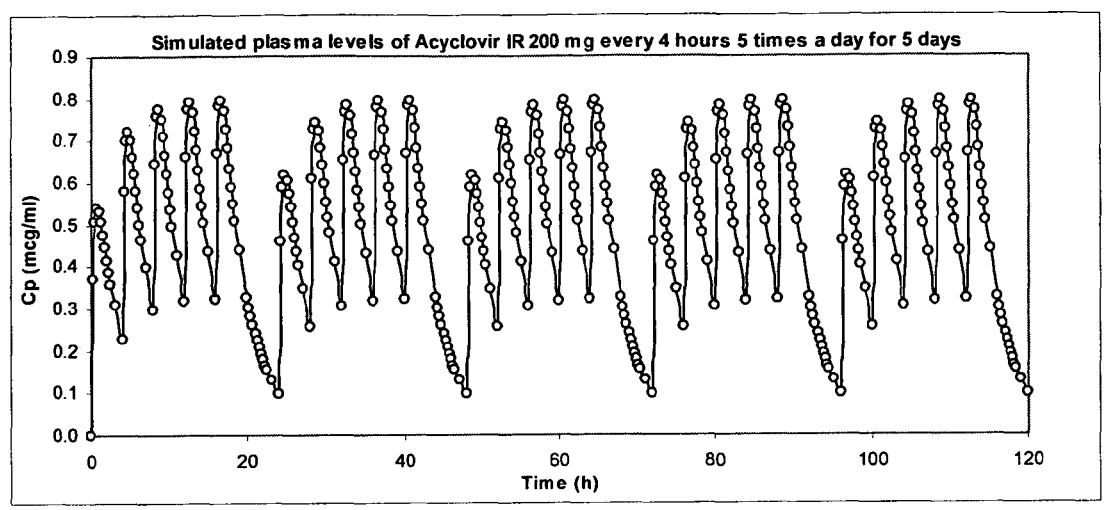

Plasma levels of multiple dose administration of Acyclovir IR 200 mg (200 mg every 4 hours, 5 times daily)[36] were simulated by super position method as shown in the FIG. 8

The FIG. 9 shows the comparison of plasma concentrations of Acyclovir IR 200 mg during the dosing day on day 1 and day 5. The difference in the maximum and minimum plasma concentrations ($C_{max}$ and $C_{min}$) achieved during day 1 and day 5 was insignificant. $C_{max}$ was about 0.80 mcg/mL and $C_{min}$ was about 0.10 mcg/mL.

Plasma Concentration Profiles of CR Formulations

Simulation was performed by two methods. First is by considering that the release of the drug and absorption follow a zero order kinetics (ER-Zero order), and the second by considering first order (ER-First order).

Comparative plasma concentration profiles are shown in FIG. 10.

The table no. 7 provides the simulated pharmacokinetic parameters of CR formulations in comparison with IR formulation. It can be observed from the data on the table above that the $C_{max}$/C12 h/C24 h plasma levels of CR formulations are close to that achieved after the administration of IR formulations.

An important biopharmaceutics factor that has to be noted here is the slow GI transit time during the second dose of the day where most of the course of the absorption is to take place in a lied down position and reduced gastrointestinal movements (when the patient is asleep). Usually this must result in a better bioavailability than the first dose (morning dose), but with a slow rate of absorption resulting in a lower $C_{max}$ as compared to the morning dose.

In-Vitro Drug Release

Since the absorption of the drug after administration of CR formulation will be independent of the intrinsic absorption rate, as the intrinsic absorption rate is far higher than drug release rate from the dosage form. So, the absorption rates used for the above simulations are considered to be reflective of the drug release. Hence the in-vitro drug release from these formulations was calculated using the general equations governing zero/first order kinetics. Table 8 and FIG. 11 present the simulated in-vitro release rate.

Preparation and Characterizations of Acyclovir Gastroretentive Tablets

Table 9 shows the composition of different gastroretentive acyclovir tablets. CARBOPOL' and PEO were selected as mucoadhesive swellable polymers for controlling the release of acyclovir. CARBOPOL® and PEO have many advantages as candidate for extended release tablets like good gel forming ability and mucoadhesive properties. The 763 mg was selected the dose of acyclovir for controlled release tablets as calculated by simulation study (Table 8 and FIG. 11). Tablets were prepared by wet granulation method and characterized for different quality control parameters.

FIG. 12-14 shows the in vitro drug release of different batches of gastroretentive tablets. Results shows that batch Acy-ER-1A, 1B and Acy-ER-3A, 3B and 3C prolong the drug release to 12 hr period of time. FIG. 15 shows the comparative graph of in vitro drug release profile of different batches with target profile generated by computer simulation study. Batch Acy-ER-3B and Acy-ER-1B were found best match with the target release profile.

Swelling is a very important characteristic of polymer that control the drug release and increase the G.I. retention of gastroretentive tablets. FIG. 15 shows the % swelling of different batches of acyclovir tablets. Result shows that batch Acy-ER-1B and Acy-ER-3B shows the significantly higher and prolong swelling to 12 hr period of time. Acy-ER-1B and 3B shows the 302.5 and 255.7% swelling after 45 min and 34.9 and 12.2% swelling after 12 hr period of time. Results are well correlated with the in vitro drug release study where similarly drug release was prolonged for 12 hr period of time. The results also shows the matrix stability to 12 hr period of time.

FIG. 16 shows the results of mucoadhesive strength measurements of different batches of gastroretentive tablets. Batch Acy-ER-1B and 3B have shown the higher mucoadhesive strengths in comparison to other batches. This invention is based on the principal of combination of swelling and mucoadhesive mechanism for preparation of gastroretentive tablets of acyclovir. Acyclovir is absorbed predominately from upper G.I tract to duodenum and jejunum region. The results of swelling and mucoadhesive measurement study showed that these both mechanisms are working in combination to develop gastroretentive tablets of this invention.

REFERENCES

1. Genta I, Conti B, Perugini P F, Pavanetto F A, Puglisi G. Bioadhesive microspheres for ophthalmic administration of acyclovir. *J Pharm Pharmacol* 1997; 49: 737-742.
2. Thanou M, Verhoef J C, Junginger H E. Chitosan and its derivatives as intestinal absorption enhancers. *Adv, Drug Deity. Rev.* 2001; 50: S91-S101.
3. Kotze, A. F., Leuben, H. L., Deleeuw, B. J., Boer, B. G., Verhoef, J. C. and Junginger, M. E. N-trimethylchitosan chloride as a potential absorption enhancer across mucosal surfaces. In vitro evaluation in intestinal epithelial cells (Caco-2). *Pharm. Res.,* 1997, 14: 1197-1202.
4. Kotze, A. F., Leuben, H. L., Leeuw, B. J., Boer, A. G., Verhoef, J. C. and Junginger, H. E. Comparison of the effect of different chitosan salts and N-trimethyl chitosan chloride on the permeability of intestinal epithelial cells (Caco-2). *J. Control. Rel.,* 1998, 51: 35-46.
5. Thanou M, Verhoef J C, Romejin S J, Nagelkerke J F, Merkus F W H M, Junginger H E. Effect of N-Trimetyl chitosan chloride, a novel absorption enhancer, on Caco-2 intestinal epithelia and the ciliary beat frequency of chicken embryo trachea. *Int J Pharm* 1999; 185(1): 73-82.
6. Rokhade A P, Shelke N B, Patil S A, Aminabhavi T M. Novel interpenetrating polymer network microspheres of chitosan and methylcellulose for controlled release of theophylline. *Carbohydrate Polymers.* 2007, 69(4): 678-687.
7. Hu F, Jiang H, Huang X, Wu X, Yuan H, Wei X, Du Y. Enhanced cellular uptake of chlorine e6 mediated by stearic-acid-grafted chitosan oligosaccharide micelles. *J Drug Targeting.* 2009, 17(5): 384-391.
8. U.S. Pat. No. 6,340,475. Extending the duration of drug release within the stomach during the fed mode.
9. US20040185105. Gastric retentive oral dosage form with restricted drug release in lower gastrointestinal tract.
10. US20070160678. Microcapsules with modified release of active principles with low solubility for oral delivery.
11. Artursson P, Lindmark T, Davis S S, Ilium L. Effect of chitosan on permeability of intestinal epithelial cells. *Pharm Research.* 1994; 11(9): 1358-1361.
12. Kotze, A. F., Thanou, M. M., Leuben, H. L., Boer, G. D., Verhoef, J. C. and Junginger, H. E. Enhancement of paracellular drug transport with highly quaternized N-trimethyl chitosan chloride in neutral environments: In vitro evaluation in intestinal epithelial cells (Caco-2). *J. Pharm. Sci.,* 1999, 88: 253-257.
13. Bernkop-Schnurch A, Schwarz V, Steininger S. Polymers with Thiol groups: A new generation of mucoadhesive polymers. *Pharm. Res.* 1999; 16(6): 876-881.
14. Bernkop-Schnurch A, Hornof M, Zoidl T. Thiolated polymers-thiomers: synthesis and in vitro evaluation of chitosan-2-iminothiolane conjugates. *Int J Pharm* 2003; 260: 229-237.
15. Maculotti K, Genta I, Perugini P, Imam M, Bernkop-Schnurch A, Pavanetto F. Preparation and in vitro evaluation of thiolated chitosan microparticles. *J Microencapsu* 2005; 22:459-470.
16. Wagstaff A G, Faulds D, Goa K L. Aciclovir: a reappraisal of its antiviral activity, pharmacokinetic properties and therapeutic efficacy. *Drugs.* 1994; 47:153-205.
17. Ruhnese M, Sandstorm F, Andersson. B. Treatment of recurrent genital herpes simplex infection with acyclovir. *J. Antimicrob. Chemother.* 1985; 16: 621-628.
18. O'Brien J J, Campoli-Richards D M. Acyclovir: an updated review of its antiviral activity, pharmacokinetic properties and therapeutic efficacy. *Drugs.* 1989; 37: 233-309.
19. Meadows K C, Dressman J B. Mechanism of acyclovir uptake in rat jejunum. *Pharm. Res.* 1990; 7(3): 299-303.
20. Wang Y M, Sato H, Adachi I, Horikoshi I. Optimization of the formulation design of chitosan microspheres containing cisplatin. *J Pharm Sci.* 1996; 85: 1204-1210.
21. Harikarnpakdee S, Lipipun V, Sutanthavibul N, Ritthidev G C. Spray dried mucoadhesive microspheres: Preparation and transport through nasal cell monolayer. *AAPS PharmSciTech* 2006; 7(1): Article 12.
22. Darwish I A, Khedr A A, Askal H F, Mahmoud R M. Simple fluorimetric method for determination of certain antiviral drugs via their oxidation with cerium(IV). *Farmaco* 2005; 60: 555-562.
23. Vyas S P, Talwar N, Karajgi J S, Jain N K. An erythrocyte based bioadhesive system for nasal delivery of propranolol. *J Control Release.* 1993; 23:231-237.
24. Jain S K, Jain R K, Chaurasia M K, Jain A K, Chalasani K B, Soni V, Jain A. Design and development of multivesicular liposomal depot delivery system for controlled systemic delivery of acyclovir sodium. *AAPS PharmSciTech* 2005; 6(1):E35-E41
25. Ebube N K, Hikal A H, Jones A B. Sustained Release of Acetaminophen from Heterogeneous Matrix Tablets: Influence of Polymer Ratio, Polymer Loading, and Coactive on Drug Release. *Pharm Dev Technol.* 1997; 2:161-170.
26. Thanoo B C, Sunny M C, Jayakrishnan A. Crosslinked chitosan microspheres: preparation and evaluation as a matrix for the controlled release of pharmaceuticals. *J Pharm. Pharmacol.* 1992; 44: 283-286.
27. Leitner V M, Walker G F, Bernkop-Schnurch A. Thiolated polymers: evidence for formation of disulphide bonds with mucus glycoproteins. *Eur J Pharm Biopharm.* 2003; 56: 207-214.
28. Mortazavi S A, Smart J D. An investigation into the role of water movement and mucus gel dehydration in mucoadhesion. *J. Control. Release.* 1993; 25:197-203.
29. Duchene D, Ponchel G. Principle and investigation of bioadhesion mechanism of solid dosage forms. *Biomaterials* 1992; 13:709-714
30. Lehr C M. From sticky stuff to sweet receptors-achievement, limits and novel approaches to bioadhesion. *Eur. J. Drug Metab. Pharmacokinet.* 1996; 21: 139-148.
31. Chng H S, Park H, Kely P, Robinson J R. Bioadhesive polymers as platforms is for oral controlled drug delivery: I. Synthesis and evaluation of some swelling, water-insoluble bioadhesive polymers. *J Pharm Sci,* 1985; 74: 399-405.

32. Bernkop-Schnurch A, Guggi D, Pinter Y. Thiolated chitosans: development and in vitro evaluation of a mucoadhesive, permeation enhancing oral drug delivery system. *J Control Release,* 2004; 94: 177-186.
33. Fischer D, Li Y, Ahlemeyer B, Krieglstein J, Kissel T. In vitro cytotoxicity testing of polycations: influence of polymer structure on cell viability and hemolysis. *Biomaterials* 2003; 24: 1121-1131
34. Guggi D, Langoth N, Hoffer M H, Wirth M, Bernkop-Schnurch A. Comparative evaluation of cytotoxicity of glucosamine-TBA conjugate and a chitosan-TBA conjugate. *Int J Pharm,* 2004; 278: 353-360.
35. Lewis L D, Fowle A S E, Bittiner S B, Bye A, Isaacs P E T. Human gastrointestinal absorption of acyclovir from tablet duodenal infusion and sipped solution; *Br J Clin Pharmacol;* 1986. 21: 459-462
36. US Prescribing information of Zovirax®.

TABLE 1

Composition of different microsphere formulation

| Form. Code | Drug Concentration (% w/w) | Polymer Concentration (% w/v) | Volume of Cross-Linker (ml) | Speed of Stirring (rpm) |
|---|---|---|---|---|
| M-CH-A1 | 0.1 | 2.0 | 0.1 | 1800 |
| M-CH-A2 | 0.2 | 2.0 | 0.1 | 1800 |
| M-CH-A3 | 0.3 | 2.0 | 0.1 | 1800 |
| M-CH-A4 | 0.4 | 2.0 | 0.1 | 1800 |
| M-CH-A5 | 0.5 | 2.0 | 0.1 | 1800 |
| M-CH-B1 | 0.3 | 1.0 | 0.1 | 1800 |
| M-CH-B2 | 0.3 | 3.0 | 0.1 | 1800 |
| M-CH-B3 | 0.3 | 4.0 | 0.1 | 1800 |
| M-CH-B4 | 0.3 | 5.0 | 0.1 | 1800 |
| M-CH-C1 | 0.3 | 2.0 | 0.2 | 1800 |
| M-CH-C2 | 0.3 | 2.0 | 0.4 | 1800 |
| M-CH-C3 | 0.3 | 2.0 | 0.6 | 1800 |
| M-CH-C4 | 0.3 | 2.0 | 0.8 | 1800 |
| M-CH-C5 | 0.3 | 2.0 | 1.0 | 1800 |
| M-CH-D1 | 0.3 | 2.0 | 1.0 | 1200 |
| M-CH-D2 | 0.3 | 2.0 | 1.0 | 1400 |
| M-CH-D3 | 0.3 | 2.0 | 1.0 | 1600 |
| M-CH-D4 | 0.3 | 2.0 | 1.0 | 2000 |
| M-TMC | 0.3 | 2.0 | 1.0 | 2000 |
| M-TCH | 0.3 | 2.0 | 1.0 | 2000 |
| *M-CA | 0.3 | 2.0 | 1.0 | |
| *M-ME | 0.3 | 2.0 | 1.0 | |

M-CH - Chitosan Microspheres;
M-TMC - Trimethyl chitosan chloride microspheres;
M-TCH - Thiolated chitosan microsphere,
M-CA = CARBOPOL ® 71G microspheres;
M-ME = METHOCEL ® K15M microsphere
*CARBOPOL ® and METHOCEL ® K15M microsphere prepared using Spray drying method
A1-A5 - Drug concentration from 0.1 to 0.5% w/w respectively
B1-B4 - Polymer concentration from 1.0 to 5.0% w/w respectively
C1-C5 - Variation in volume of cross linker from 0.2 to 1.0 ml respectively
D1-D4 - Variation in speed of stirring from 1200 to 2000 rpm respectively

TABLE 2

Characterization and optimization of different microsphere formulation

| Form. Code | Surface | Shape | Particle size | % Entrapment efficiency |
|---|---|---|---|---|
| M-CH-A1 | − | Aggregation | 15.0 ± 0.3 | 55 ± 1.8 |
| M-CH-A2 | − | Aggregation | 17.2 ± 0.5 | 64.2 ± 2.8 |
| M-CH-A3 | − | Aggregation | 20.8 ± 0.9 | 74.5 ± 3.1 |
| M-CH-A4 | − | Aggregation | 20.0 ± 0.8 | 68.7 ± 2.9 |
| M-CH-A5 | − | Aggregation | 19.5 ± 0.6 | 60.9 ± 2.5 |
| M-CH-B1 | − | Aggregation | 12.3 ± 0.1 | 67 ± 2.8 |
| M-CH-B2 | + | Discrete | 18.1 ± 0.5 | 85.1 ± 3.9 |
| M-CH-B3 | + | Discrete | 15.0 ± 0.3 | 70.9 ± 2.9 |
| M-CH-B4 | + | Discrete | 14.9 ± 0.2 | 65.0 ± 2.5 |
| M-CH-C1 | + | Discrete | 19.5 ± 0.89 | 90.0 ± 4.1 |
| M-CH-C2 | + | Discrete | 19.0 ± 0.82 | 88.5 ± 3.7 |
| M-CH-C3 | + | Discrete | 19.2 ± 0.84 | 88.0 ± 3.6 |
| M-CH-C4 | + | Discrete | 18.9 ± 0.79 | 89.4 ± 3.9 |
| M-CH-C5 | + | Discrete | 18.8 ± 0.75 | 92.0 ± 4.3 |
| M-CH-D1 | ++ | Discrete | 21.3 ± 0.9 | 87.7 ± 3.7 |
| M-CH-D2 | ++ | Discrete | 19.1 ± 0.8 | 87.2 ± 3.6 |
| M-CH-D3 | ++ | Discrete | 17.5 ± 0.7 | 87.0 ± 3.5 |
| M-CH-D4 | ++ | Discrete | 12.5 ± 0.3 | 88.0 ± 2.6 |
| M-TMC | ++ | Discrete | 11.2 ± 0.4 | 91.3 ± 4.5 |
| M-TCH | ++ | Discrete | 21.3 ± 1.0 | 86.8 ± 3.1 |
| M-CA | + | Aggregate | 20.6 ± 1.2 | 91.4 ± 4.2 |
| M-ME | + | Aggregate | 17.8 ± 1.5 | 77.3 ± 4.2 |

Value represent as mean ± SD (n = 3)
−Rough
+Smooth
++Perfectly smooth

TABLE 3

In vitro characterizations of mucoadhesive microspheres

| Formulation Code | Production Yield (%) | Particle Size (μm) | Entrapment efficiency (%) | Adhesion Time (Hrs) |
|---|---|---|---|---|
| M-CH | 74.5 ± 3.5 | 18.2 ± 0.8 | 88.0 ± 2.6 | 3.1 ± 0.4 |
| M-TMC | 72.4 ± 2.8 | 11.2 ± 0.4 | 91.3 ± 4.5 | 4.9 ± 0.6 |
| M-TCH | 76.3 ± 3.8 | 21.3 ± 1.0 | 86.8 ± 3.1 | 8.0 ± 0.8 |
| M-CA | 69.4 ± 4.1 | 20.6 ± 1.2 | 91.4 ± 4.2 | 0.2 ± 0.1 |
| M-ME | 54.1 ± 3.0 | 17.8 ± 1.5 | 77.3 ± 4.2 | 1.1 ± 0.2 |

Data represents as mean ± SD (n = 3)

TABLE 4

GI distribution of 6-CF in rat gastrointestinal tract after administration as solution and mucoadhesive microspheres

| | % Dose recovered | | | | | | | | | | | | | | |
|---|---|---|---|---|---|---|---|---|---|---|---|---|---|---|---|
| | 6-CF solution | | | | | M-TCH | | | | | M-CH | | | | |
| Section no. | 2 hr | 4 hr | 6 hr | 8 hr | 10 hr | 2 hr | 4 hr | 6 hr | 8 hr | 10 hr | 2 hr | 4 hr | 6 hr | 8 hr | 10 hr |
| 1. Stomach | 52.2 ± 2.3 | 3.5 ± 0.2 | 0 | 0 | 0 | 22.3 ± 3.1 | 12.6 ± 1.4 | 6.8 ± 0.6 | 2.1 ± 0.3 | 0 | 23.8 ± 2.5 | 11.2 ± 0.8 | 4.3 ± 0.5 | 0 | 0 |
| 2. Duodenum | 10.9 ± 1.4 | 19.5 ± 3.2 | 0 | 0 | 0 | 15.5 ± 1.6 | 16.3 ± 1.7 | 12.4 ± 1.1 | 7.8 ± 0.7 | 3.8 ± 0.2 | 14.2 ± 1.3 | 13.1 ± 1.2 | 10.2 ± 1.0 | 5.6 ± 0.5 | 1.2 ± 0.2 |
| 3. Jejunum | 0 | 10.6 ± 1.2 | 0 | 0 | 0 | 13.9 ± 1.4 | 14.1 ± 1.3 | 14.2 ± 1.4 | 10.1 ± 1.2 | 9.1 ± 0.7 | 10.8 ± 1.1 | 12.6 ± 1.2 | 10.6 ± 1.1 | 8.9 ± 0.7 | 4.2 ± 0.5 |

TABLE 4-continued

GI distribution of 6-CF in rat gastrointestinal tract after administration as solution and mucoadhesive microspheres

| 4. Jejunum | 0 | 5.8 ± 0.6 | 6.9 ± 0.7 | 0 | 0 | 6.4 ± 0.5 | 11.2 ± 1.2 | 15.5 ± 1.6 | 14.8 ± 1.6 | 13.1 ± 1.5 | 3.6 ± 0.4 | 7.8 ± 0.6 | 15.4 ± 1.4 | 12.1 ± 1.0 | 7.5 ± 1.0 |
| 5. Jejunum | 0 | 0 | 3.9 ± 0.4 | 0 | 0 | 0 | 8.4 ± 0.9 | 15.1 ± 1.5 | 18.6 ± 2.0 | 17.5 ± 1.8 | 0 | 4.2 ± 0.5 | 9.6 ± 0.8 | 17.6 ± 1.8 | 13.5 ± 1.2 |
| 6. Ileum | 0 | 0 | 0 | 5.9 ± 0.7 | 0 | 0 | 4.2 ± 0.4 | 10.8 ± 1.1 | 15.5 ± 1.6 | 11.7 ± 1.2 | 0 | 1.5 ± 0.2 | 7.3 ± 0.6 | 15.2 ± 1.4 | 10.7 ± 1.0 |
| 7. Remaining Intestine | 0 | 0 | 0 | 0 | 0 | 0 | 1.1 ± 0.1 | 10.2 ± 1.0 | 12.8 ± 1.2 | 12.1 ± 1.4 | 0 | 0 | 6.4 ± 0.5 | 13.6 ± 1.2 | 8.7 ± 0.7 |

| | % Dose recovered | | | | | | | | | | | | | | |
|---|---|---|---|---|---|---|---|---|---|---|---|---|---|---|---|
| | M-CA | | | | | M-ME | | | | | M-TMC | | | | |
| Section no. | 2 hr | 4 hr | 6 hr | 8 hr | 10 hr | 2 hr | 4 hr | 6 hr | 8 hr | 10 hr | 2 hr | 4 hr | 6 hr | 8 hr | 10 hr |
| 1. Stomach | 17.2 ± 1.5 | 5.4 ± 0.5 | 0 | 0 | 0 | 14.2 ± 1.2 | 0 | 0 | 0 | 0 | 22.6 ± 1.8 | 10.1 ± 0.8 | 5.2 ± 1.8 | 0 | 0 |
| 2. Duodenum | 7.5 ± 0.9 | 7.5 ± 0.6 | 0 | 0 | 0 | 5.6 ± 0.5 | 2.1 ± 0.3 | 0 | 0 | 0 | 17.5 ± 1.5 | 12.4 ± 1.1 | 11.1 ± 1.0 | 7.1 ± 0.6 | 5.2 ± 0.3 |
| 3. Jejunum | 0 | 5.8 ± 0.5 | 6.8 ± 0.7 | 0 | 0 | 0 | 3.5 ± 0.5 | 0 | 0 | 0 | 15.9 ± 1.2 | 13.6 ± 1.4 | 14.5 ± 1.3 | 8.2 ± 0.8 | 7.2 ± 0.6 |
| 4. Jejunum | 0 | 3.7 ± 0.4 | 5.8 ± 0.5 | 5.4 ± 0.4 | 2.5 ± 0.3 | 0 | 4.0 ± 0.5 | 8.0 ± 0.9 | 0 | 0 | 10.1 ± 1.0 | 17.5 ± 1.5 | 16.3 ± 1.7 | 10.1 ± 1.2 | 10.1 ± 0.9 |
| 5. Jejunum | 0 | 2.1 ± 0.2 | 4.4 ± 0.3 | 6.4 ± 0.5 | 0 | 0 | 3.2 ± 0.4 | 5.0 ± 0.5 | 0 | 0 | 0 | 7.5 ± 0.6 | 10.5 ± 0.7 | 11.5 ± 1.2 | 14.5 ± 1.1 |
| 6. Ileum | 17.2 ± 1.5 | 5.4 ± 0.5 | 0 | 0 | 0 | 14.2 ± 1.2 | 0 | 0 | 0 | 0 | 5.1 ± 0.4 | 12.3 ± 1.1 | 13.1 ± 1.4 | 17.1 ± 1.5 | |
| 7. Remaining Intestine | 7.5 ± 0.9 | 7.5 ± 0.6 | 0 | 0 | 0 | 5.6 ± 0.5 | 2.1 ± 0.3 | 0 | 0 | 0 | 3.5 ± 0.2 | 13.5 ± 1.4 | 15.2 ± 1.5 | 20.6 ± 1.9 | |

Data represents as mean ± SD (n = 3)

TABLE 5

Results of pharmacokinetic and hemolytic toxicity assay of different microsphere formulations of acyclovir

| Form. Code | *AUC (ng. hour/ml) | *Cmax (ng) | *MRT (hr) | **RB (%) | % Hemolysis |
|---|---|---|---|---|---|
| Drug solution | 281.7 ± 28 | 53.07 ± 6.8 | 5.4 ± 0.5 | 100 | 10.2 ± 1.4 |
| M-CH | 885.8 ± 72 | 54.87 ± 8.2 | 12.4 ± 1.2 | 314.4 ± 13 | 20.1 ± 2.0 |
| M-TMC | 1335.5 ± 58 | 62.00 ± 8.9 | 13.1 ± 1.4 | 474.1 ± 16 | 27.2 ± 1.8 |
| M-TCH | 1090.7 ± 51 | 59.69 ± 10.1 | 17.9 ± 1.8 | 387.1 ± 18 | 13.1 ± 1.2 |
| M-CA | 727.8 ± 45 | 47.69 ± 6.8 | 11.6 ± 1.1 | 258.3 ± 12 | 26.2 ± 3.4 |
| M-ME | 510.5 ± 35 | 33.33 ± 5.8 | 11.3 ± 1.0 | 181.2 ± 10 | 22.0 ± 2.8 |

*Analyzed by WinNolin software
**RB Relative Bioavailability.
Data represents as mean ± SD (n = 3)

TABLE 6

Pharmacokinetic parameters of acyclovir

| Parameter | Value | Remarks |
|---|---|---|
| Time to maximum plasma concentration ($t_{max}$) | 1.4 h | From Ref. 35 |
| Apparent elimination half-life ($t_{1/2}$) | 2.3 h | From Ref. 35 |
| Area under plasma concentration profile (AUC) | 3.3075 mcg*h/mL | From Ref. 35 |
| Elimination rate constant ($k_{el}$) | 0.3010 $h^{-1}$ | Calculated from $t_{1/2}$ |
| Absorption rate ($k_a$) | 3.2894 $h^{-1}$ | Calculated from $t_{max}$. Since, it is an IR product, it is assumed that almost 99% of absorption is complete at $t_{max}$ |
| Apparent volume of distribution ($V_z$) | 401.38 L | Calculated from dose, AUC and $k_{el}$ |

TABLE 7

Simulated pharmacokinetic parameters of CR formulations in comparison with IR formulation.

| | Day 1 | | | Day 5 | | |
|---|---|---|---|---|---|---|
| Formulation | IR | CR-Zero Order | CR-First Order | IR | CR-Zero Order | CR-First Order |
| Dose (mg) | 1000 | 723 | 723 | 723 | 1000 | 723 |
| Absorption rate | 3.2894 $h^{-1}$ | 100 mg/h | 0.2556 $h^{-1}$ | — | — | — |
| $C_{max}$ (mcg/mL) | 0.80 | 0.80 | 0.88 | 0.80 | 0.80 | 0.89 |
| $C_{12h}$ (mcg/mL) | 0.32 | 0.31 | 0.25 | 0.32 | 0.32 | 0.27 |
| $C_{24h}$ (mcg/mL) | 0.10 | 0.32 | 0.27 | 0.10 | 0.32 | 0.27 |
| $AUC_t$ (mcg*h/mL) | 11.05 | 13.88 | 13.69 | — | — | — |
| % AUC | 100 | 126 | 124 | — | — | — |

TABLE 8

Predicated in vitro drug release profile of Acyclovir CR formulation

| Time (h) | % Drug Released | |
|---|---|---|
| | Zero order | First order |
| 0 | 0.0 | 0.0 |
| 1 | 11.1 | 22.6 |
| 2 | 22.2 | 40.0 |
| 3 | 33.3 | 53.6 |
| 4 | 44.4 | 64.0 |
| 5 | 55.6 | 72.1 |
| 6 | 66.7 | 78.4 |
| 7 | 77.8 | 83.3 |
| 8 | 88.9 | 87.1 |
| 9 | 100.0 | 90.0 |

TABLE 9

Composition of sustained release gastroretentive tablets of acyclovir

| Batch no. | Acy-ER-1A | Acy-ER-1B | Acy-ER-2A | Acy-ER-2B | Acy-ER-3A | Acy-ER-3B | Acy-ER-3C |
|---|---|---|---|---|---|---|---|
| Acyclovir | 763.37 | 763.37 | 763.37 | 763.37 | 763.37 | 763.37 | 763.37 |
| CARBOPOL ® 974P | 100 | 150 | — | — | 50 | 75 | 25 |
| *PEO | 100 | 50 | 50 | 25 | 75 | | |
| AVICEL ® PH 101 | 93.83 | 93.83 | 43.83 | 93.83 | 143.83 | 93.83 | 93.83 |
| POVIDONE ® K30 | 30 | 30 | 30 | 30 | 30 | 30 | 30 |
| Magnesium stearate | 7.5 | 7.5 | 7.5 | 7.5 | 7.5 | 7.5 | 7.5 |
| Colloidal silicon oxide | 5.0 | 5.0 | 5.0 | 5.0 | 5.0 | 5.0 | 5.0 |
| Ethanol | q.s. | q.s. | q.s. | q.s. | q.s. | q.s. | q.s. |
| Total weight | 1000 mg | 1000 mg | 1000 mg | 1000 mg | 1000 mg | 1000 mg | |

*Polyethylene oxide

The invention claimed is:

1. A controlled release tablet containing no solubilizer, wherein the controlled release tablet is capable of releasing the pharmaceutically active agent at a rate of between 80-100% in 12 hours in a first order rate of release in a USP type 2 dissolution test,
    the tablet comprising,
    for every 1000 mg of the dosage form,
    Acyclovir in an amount of 763.37 mg, a high molecular weight polymer of acrylic acid crosslinked with allyl ethers of pentaerythritol in an amount of 75 mg, Polyethylene oxide in an amount of 25 mg, microcrystalline cellulose in amount 93.83 mg, polyvinylpyrrolidone having a viscosity of 44000-54000 cps in an amount of 30 mg, Magnesium stearate in an amount of 7.5 mg, and Colloidal silicon dioxide 5.0 mg.

2. A method of administering acyclovir to a patient in need thereof, comprising orally administering a therapeutically effective amount of the acyclovir in a controlled release tablet according to claim 1 to the patient.

3. A process of making a controlled release tablet according to claim 1,
    the process comprising making wet granulation of the high molecular weight polymer of acrylic acid crosslinked with allyl ethers of pentaerythritol, the Polyethylene oxide, the Acyclovir, the microcrystalline cellulose, the polyvinylpyrrolidone having a viscosity of 44000-54000 cps, and the Magnesium stearate; adding the colloidal silicon; and pressing into a tablet.

* * * * *